United States Patent [19]
Kami et al.

[11] Patent Number: 5,176,140
[45] Date of Patent: Jan. 5, 1993

[54] ULTRASONIC PROBE

[75] Inventors: Kuniaki Kami, Hachioji; Masashi Abe, Hino; Masao Izawa, Hachioji; Takanao Fujimura, Kodaira; Yukihiko Sawada, Hachioji; Masaaki Hayashi, Hachioji; Shuichi Takayama, Hachioji; Takashi Tsukaya, Hachioji; Takeaki Nakamura, Hino; Masanori Hamazaki, Hachioji; Takahiro Echizenya, Hachioji; Yoshihisa Taniguchi, Hachioji; Hironobu Aoki, Chino; Fukashi Yoshizawa, Okaya; Yoshiro Nishimura, Okaya; Hiroshi Suzushima, Okaya, all of Japan

[73] Assignee: Olympus Optical Co., Ltd., Tokyo, Japan

[21] Appl. No.: 567,392

[22] Filed: Aug. 14, 1990

[30] Foreign Application Priority Data

| Aug. 14, 1989 | [JP] | Japan | 1-207818 |
| Aug. 15, 1989 | [JP] | Japan | 1-209632 |
| Nov. 21, 1989 | [JP] | Japan | 1-304182 |
| Nov. 21, 1989 | [JP] | Japan | 1-304183 |
| Apr. 9, 1990 | [JP] | Japan | 2-92085 |
| Apr. 9, 1990 | [JP] | Japan | 2-92086 |
| Apr. 18, 1990 | [JP] | Japan | 2-100265 |
| Jul. 13, 1990 | [JP] | Japan | 2-184332 |
| Jul. 16, 1990 | [JP] | Japan | 2-185393 |

[51] Int. Cl.⁵ ............................. A61B 8/00
[52] U.S. Cl. ................ 128/662.03; 310/335; 310/336; 310/327; 73/597
[58] Field of Search .......... 128/660.01, 661.01, 128/662.03, 662.06; 310/335, 336, 327; 73/597, 598, 599

[56] References Cited

U.S. PATENT DOCUMENTS

| 4,101,795 | 7/1978 | Fukumoto et al. | 128/662.03 |
| 4,168,628 | 9/1979 | Vilkomerson | 128/661.01 |
| 4,184,094 | 1/1980 | Kopel | 128/662.03 |
| 4,385,255 | 5/1983 | Yamaguchi et al. | 310/335 |
| 4,446,395 | 5/1984 | Hadjicostis | 310/327 |
| 4,773,267 | 9/1988 | Abts | 73/597 |
| 5,002,058 | 3/1991 | Martinelli | 128/662.06 |

Primary Examiner—Francis Jaworski
Assistant Examiner—George Manuel
Attorney, Agent, or Firm—Stevens, Davis, Miller & Mosher

[57] ABSTRACT

In an ultrasonic probe for use in ultrasonic endoscope, ultrasonic diagnosing apparatus and other ultrasonic apparatuses, an ultrasonic vibrator is arranged in a recess formed in a cylindrical housing and is secured thereto such that portions of first and second electrodes are exposed out of the recess. First and second lead wires are embedded in the housing such that tips of the lead wires are exposed within connecting areas formed in the housing in communication with the recess. The tips of the first and second lead wires are connected to first and second electrodes of the ultrasonic vibrator with the aid of conductive members made of solder, conductive paste or conductive adhesive agent. The other end of the first and second lead wires are extended from the same end face of the cylindrical housing.

27 Claims, 35 Drawing Sheets

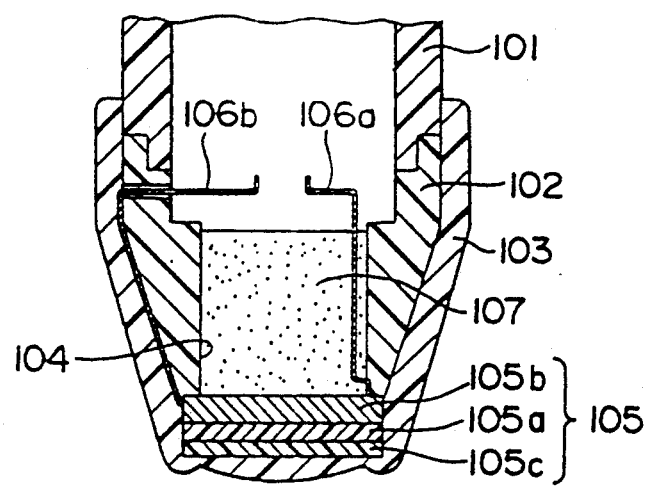
FIG_1
PRIOR ART
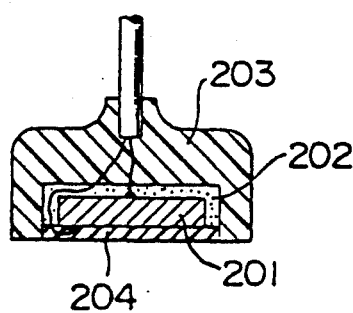
FIG_2
PRIOR ART

FIG_3
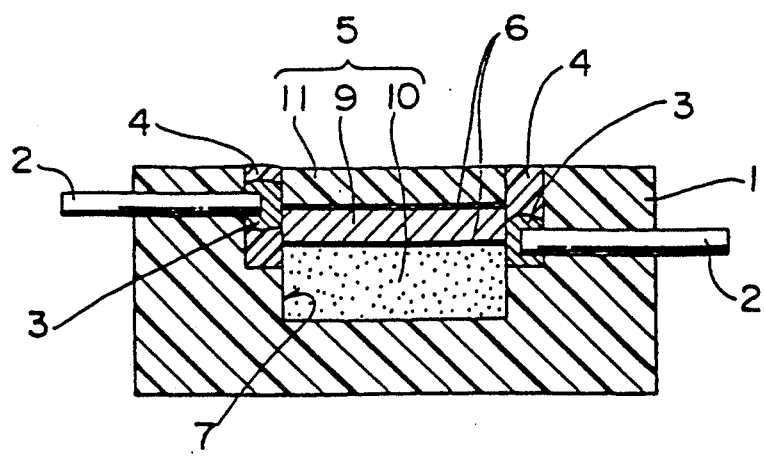
FIG_4
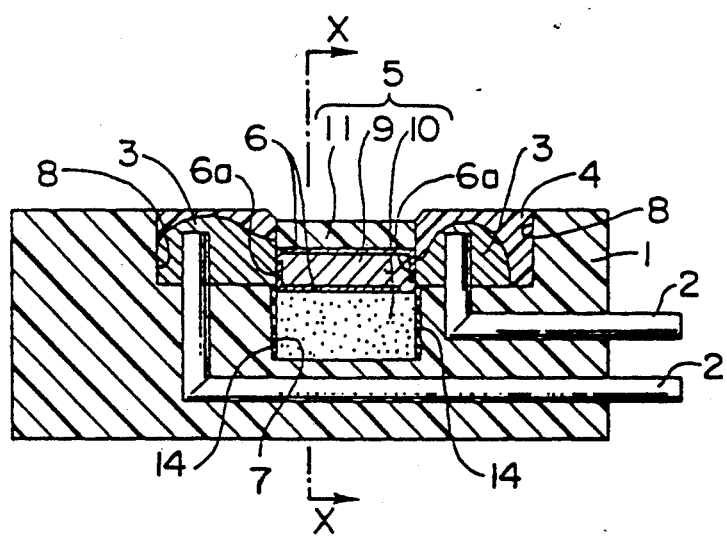
FIG_5
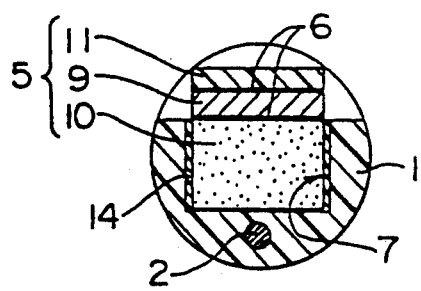
FIG_6
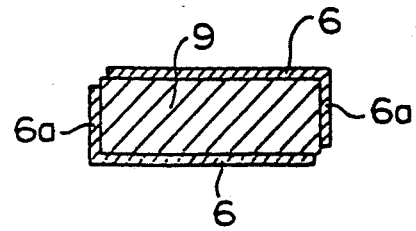

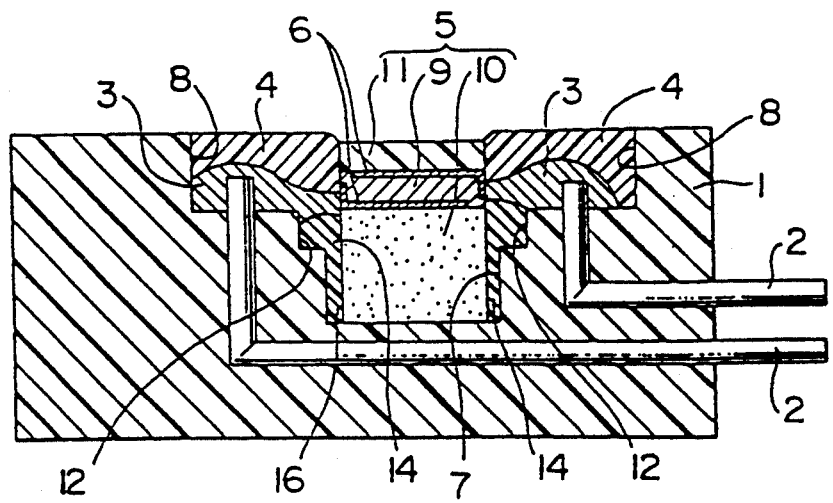
FIG_7
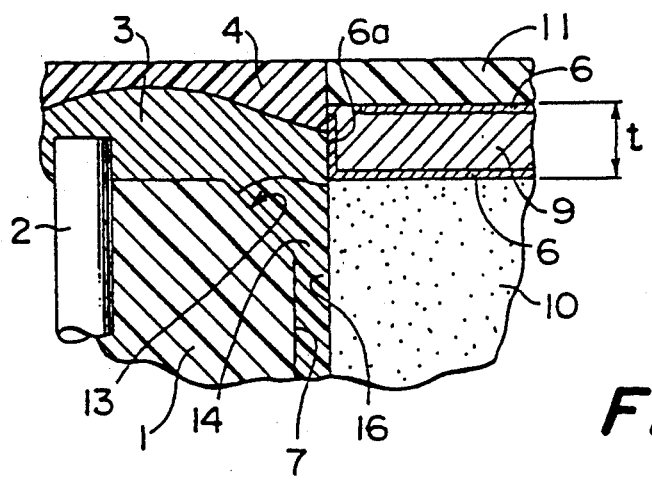
FIG_8
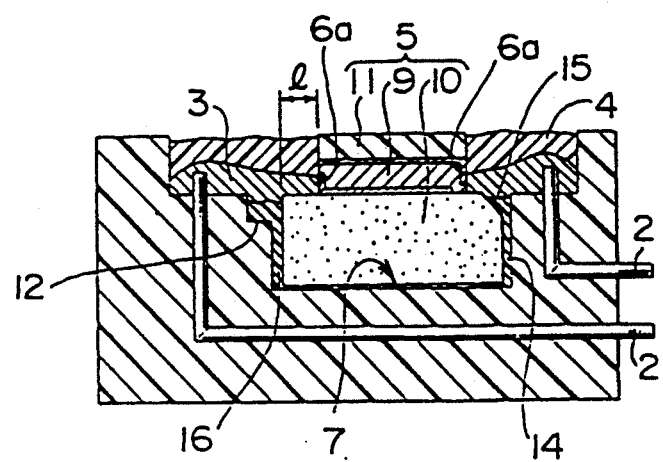
FIG_9

FIG._11
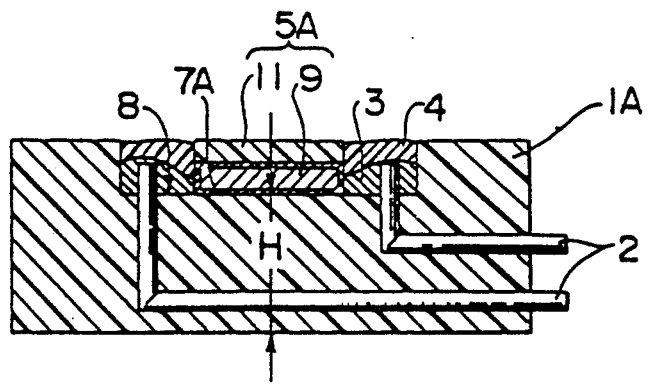
FIG._12
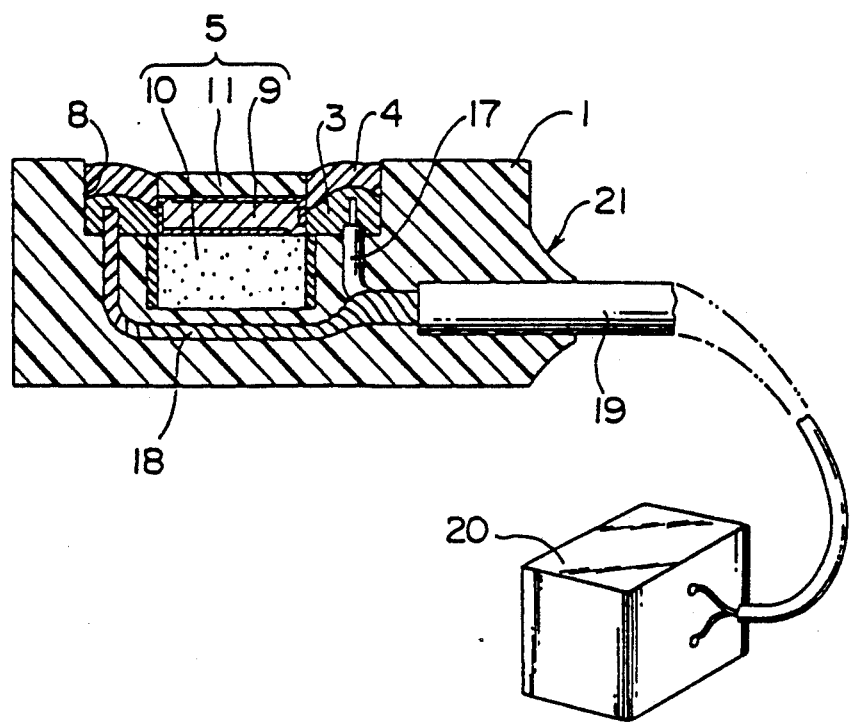

FIG_13
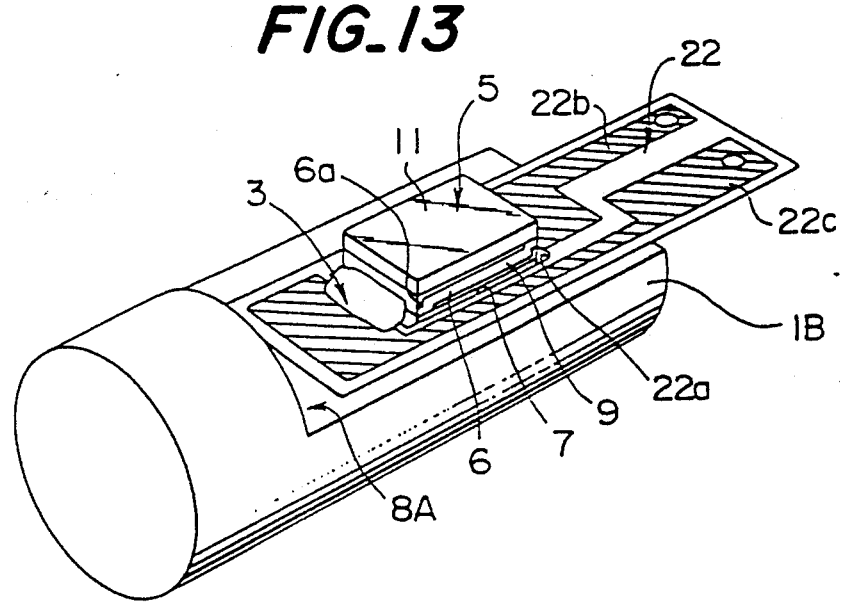
FIG_14
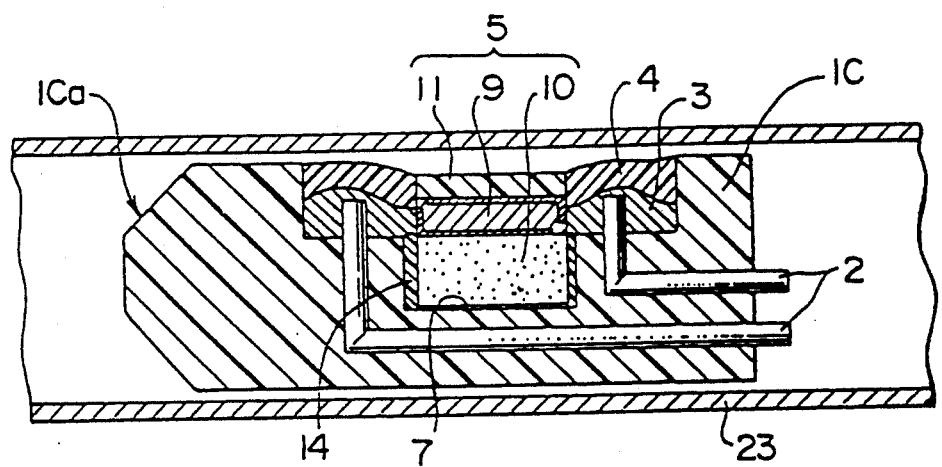
FIG_15
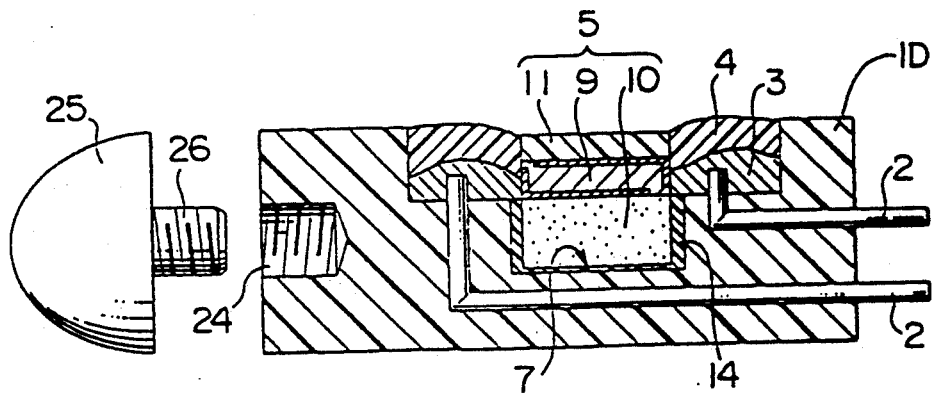

FIG_16
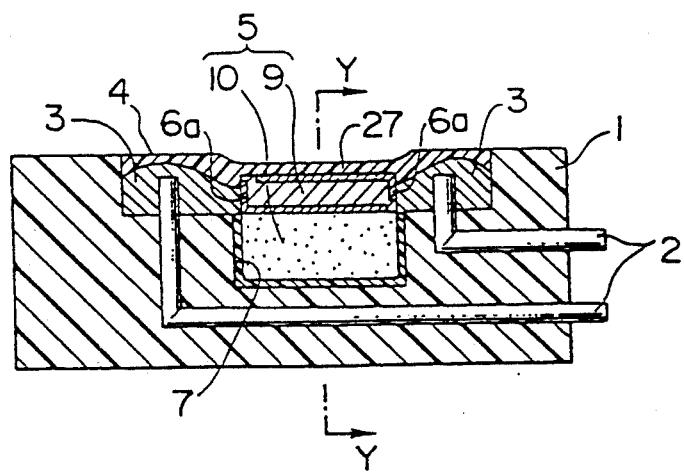
FIG_17
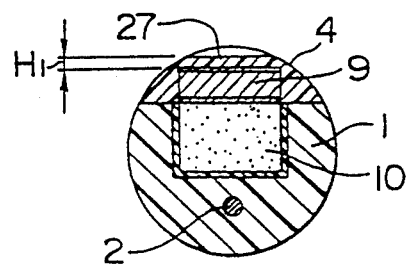
FIG_18
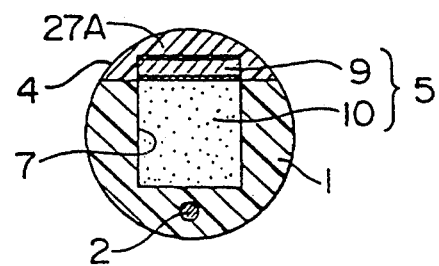

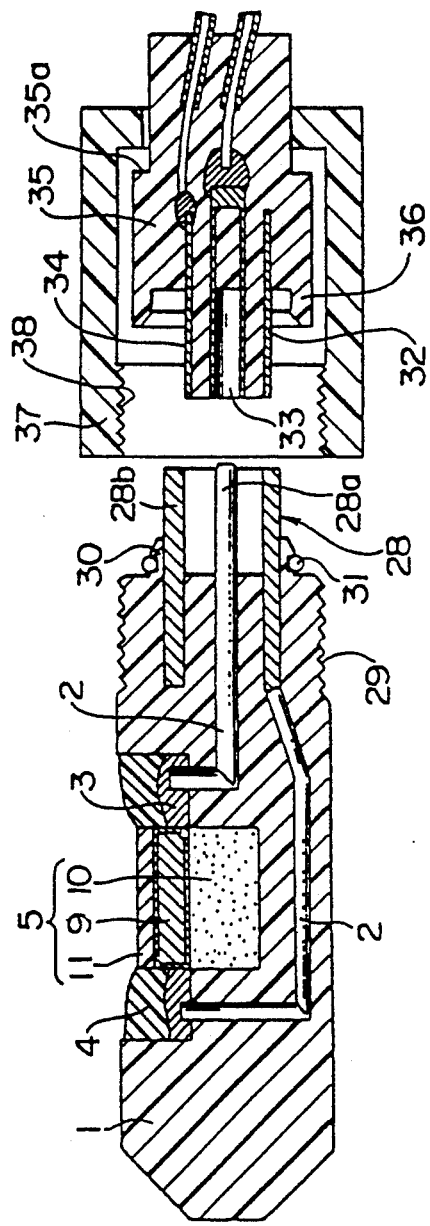
FIG._19
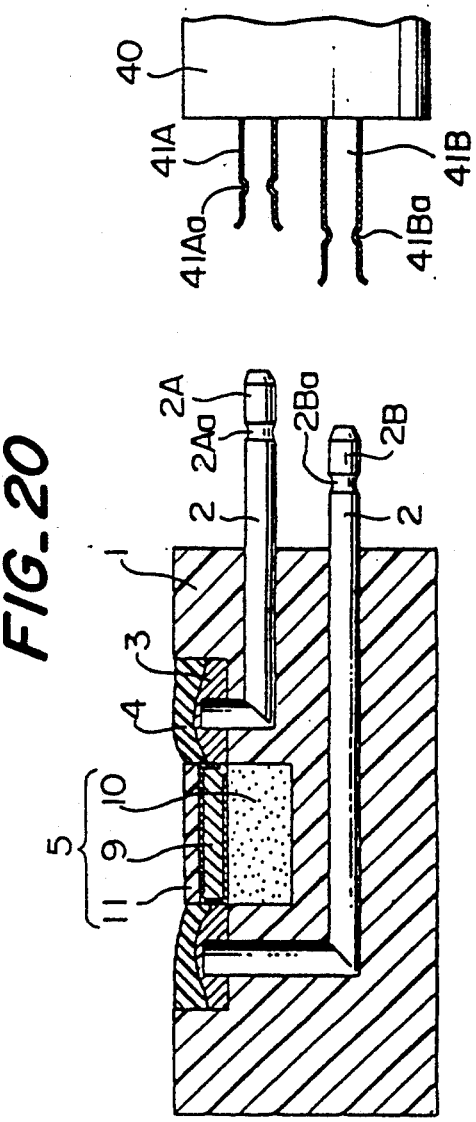
FIG._20

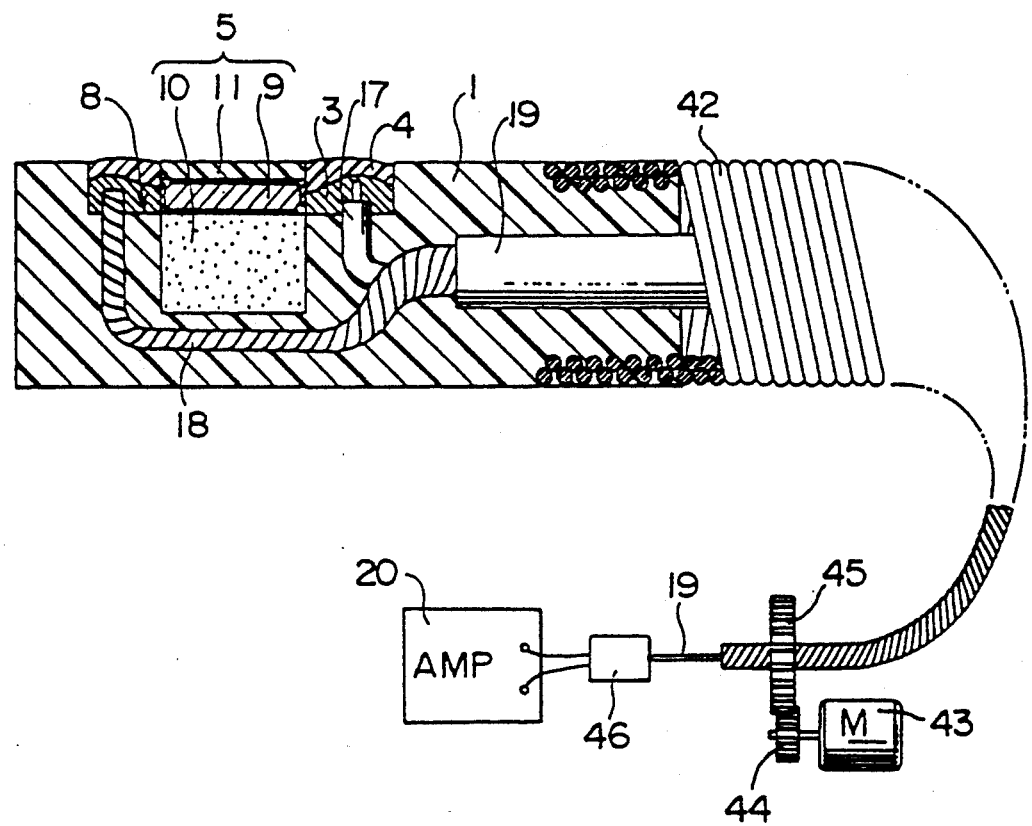
FIG_21

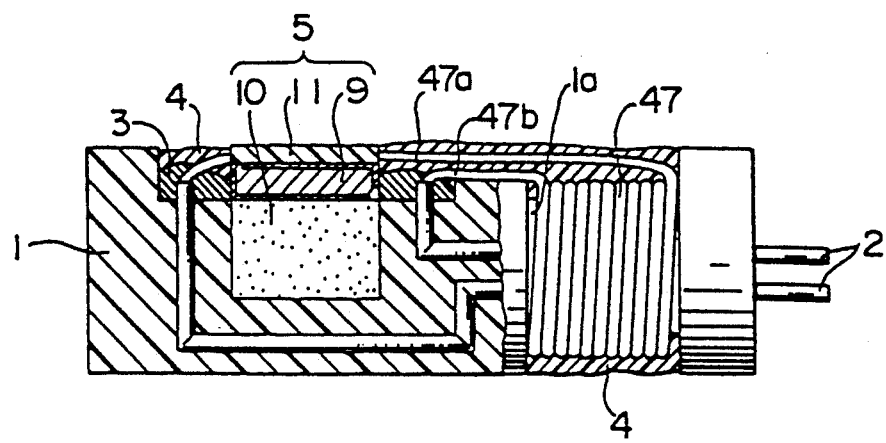
FIG_22
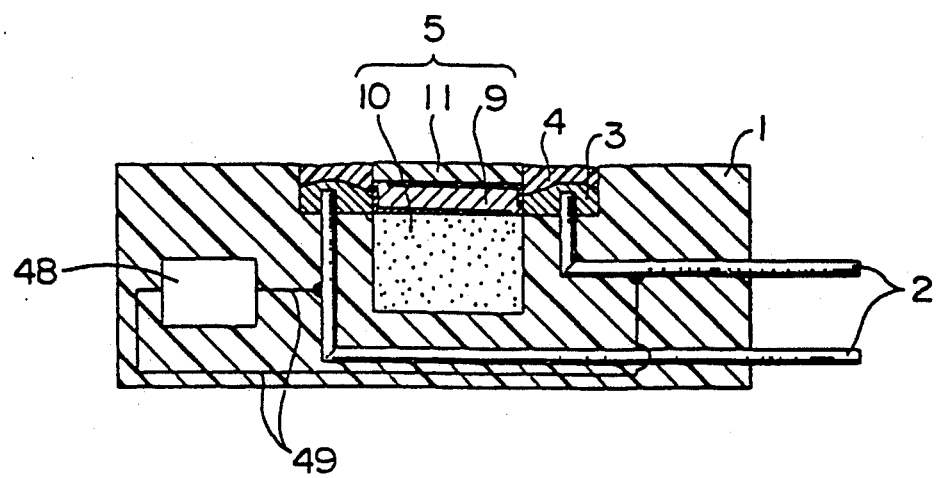
FIG_23

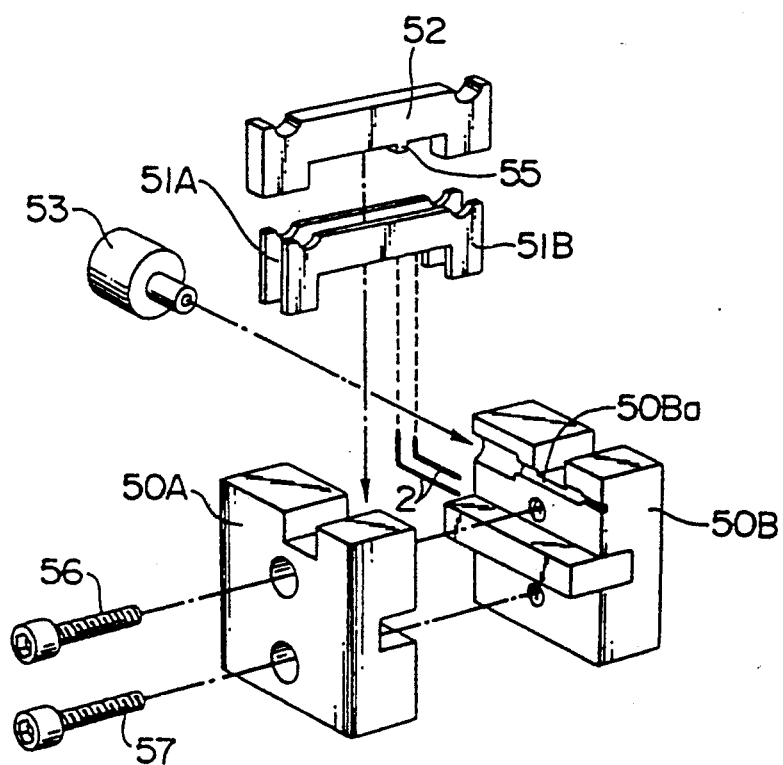
FIG_25

FIG_30

FIG_31

FIG_34
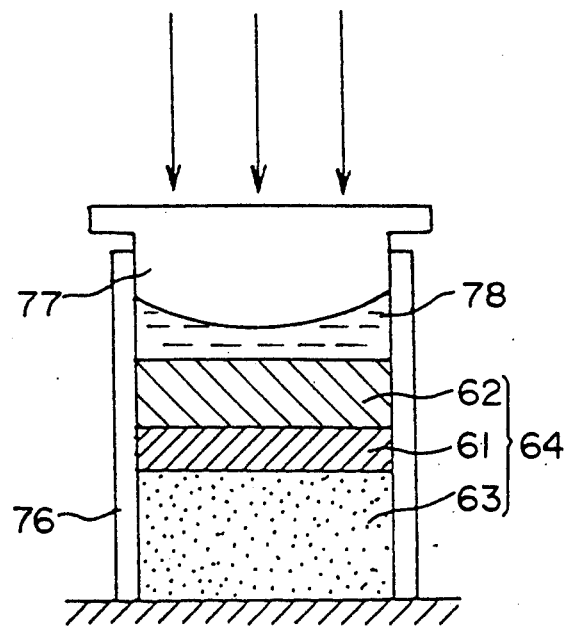
FIG_35
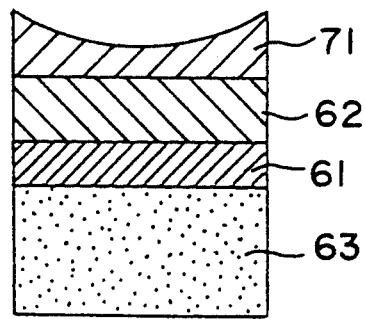

FIG_38A
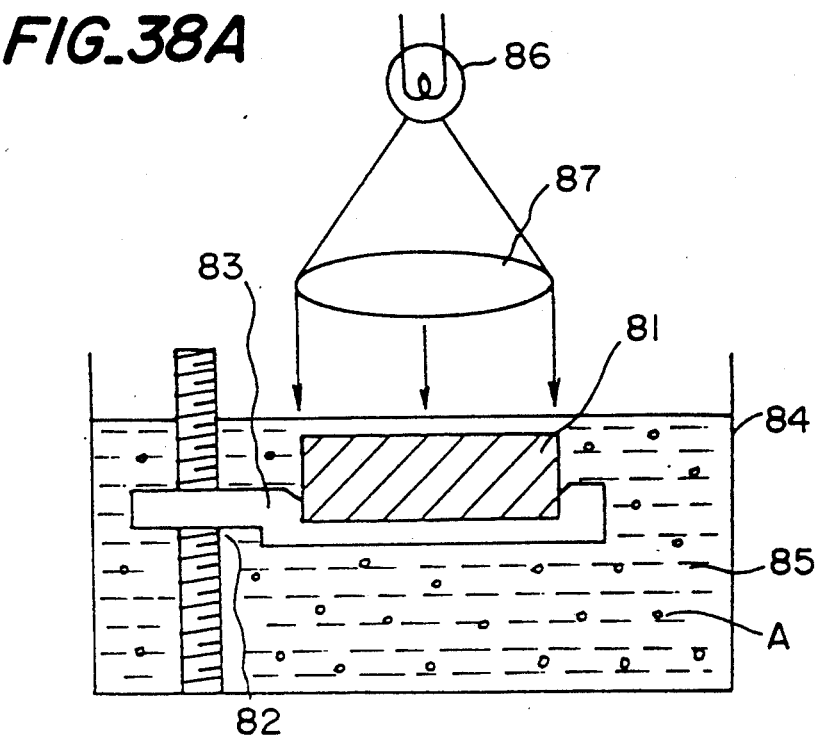
FIG_38B
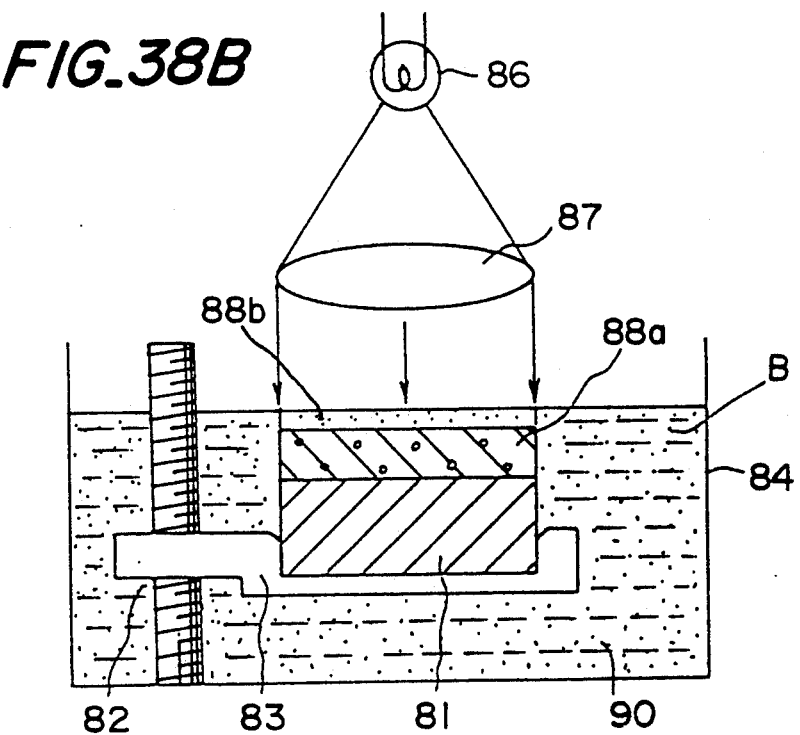

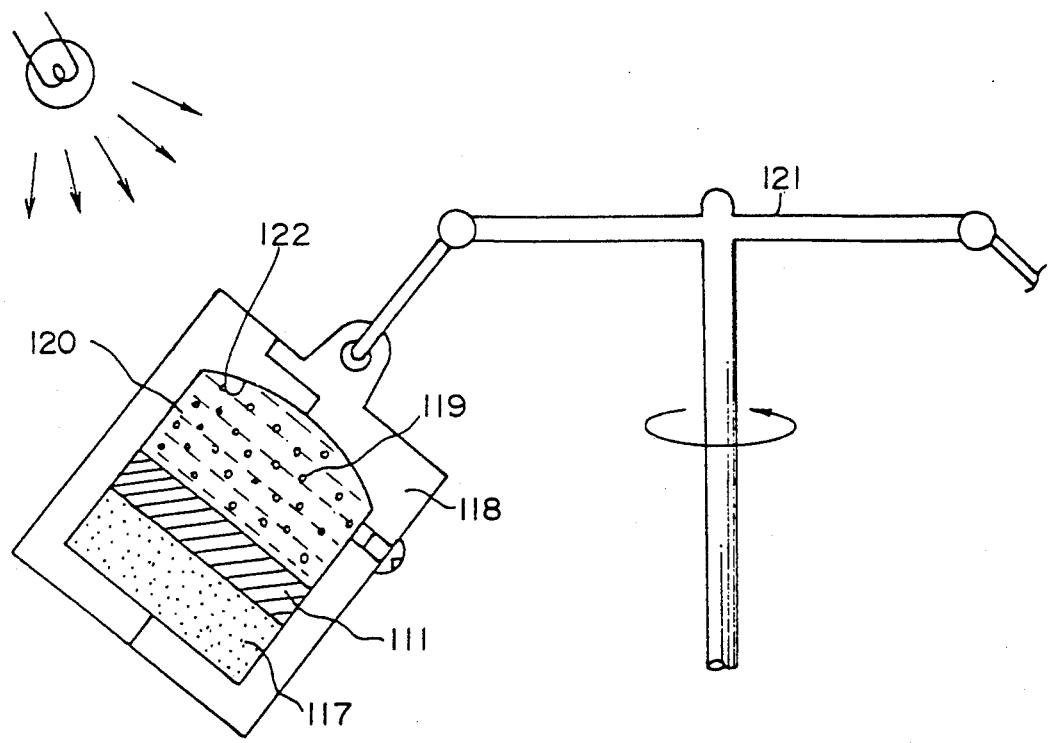
FIG_39

FIG_40
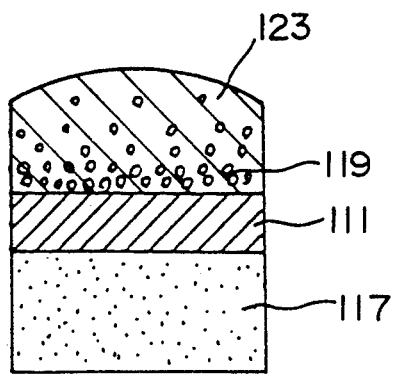
FIG_41
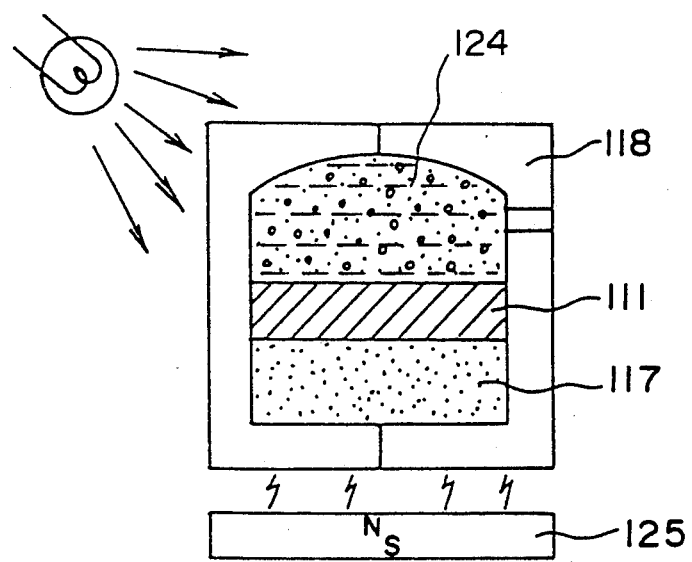

FIG_42
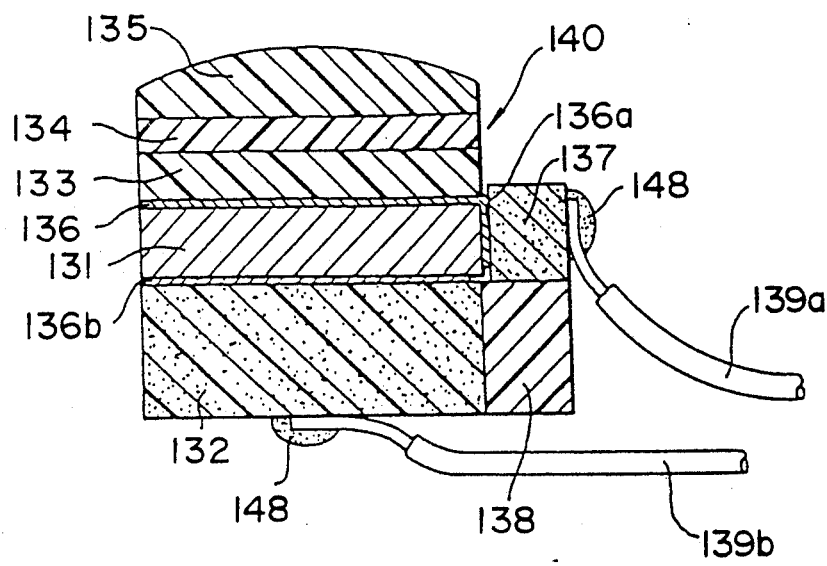
FIG_43
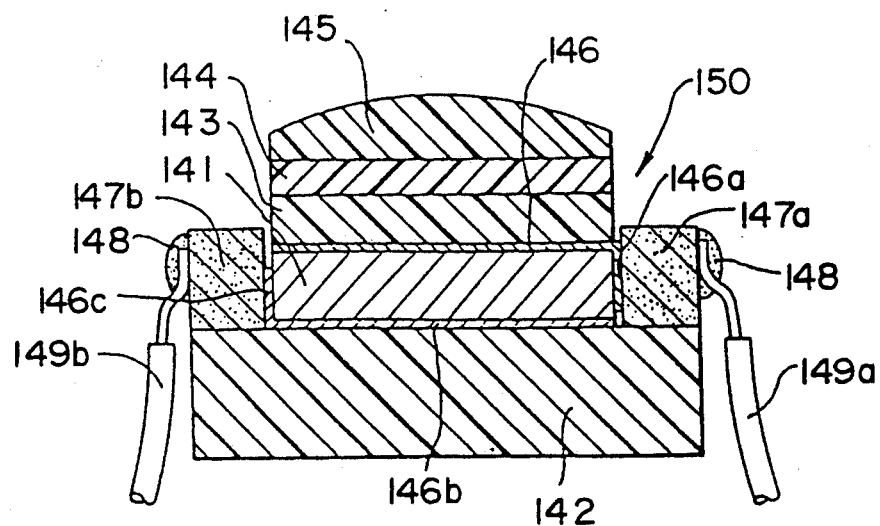

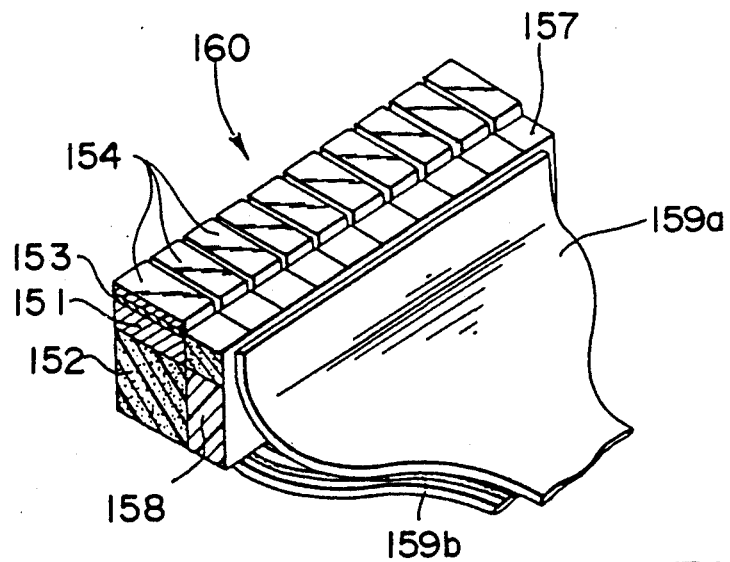
FIG_44
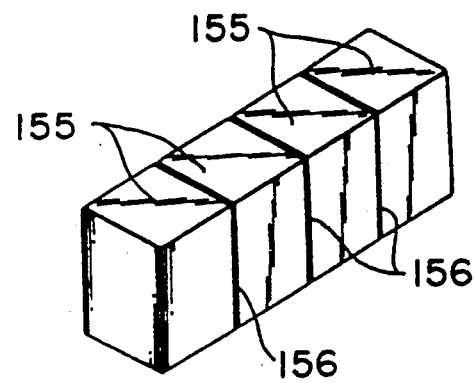
FIG_45
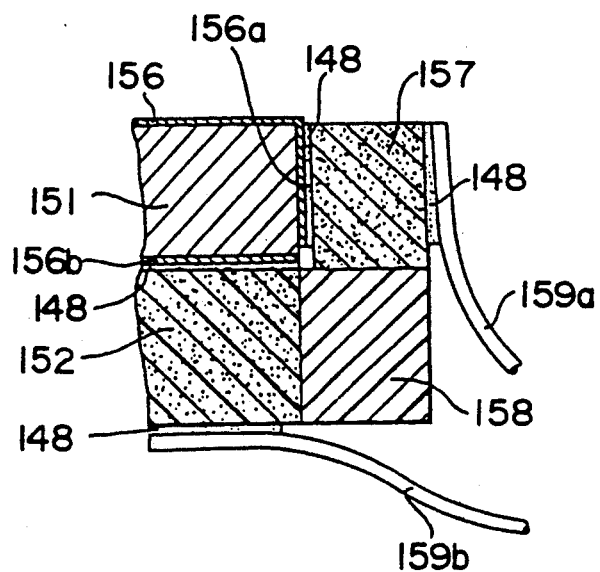
FIG_46

FIG_47
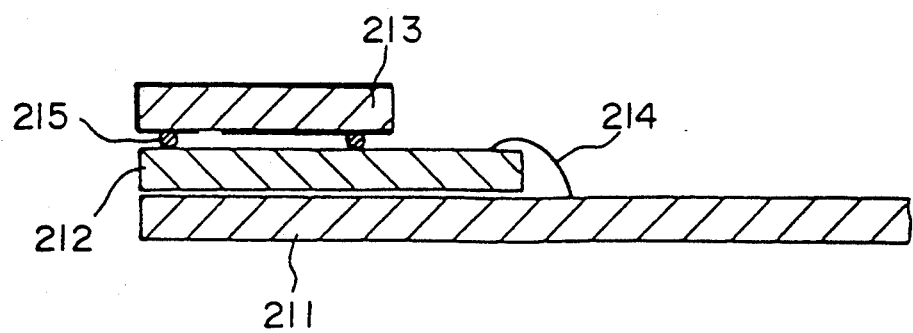
FIG_48
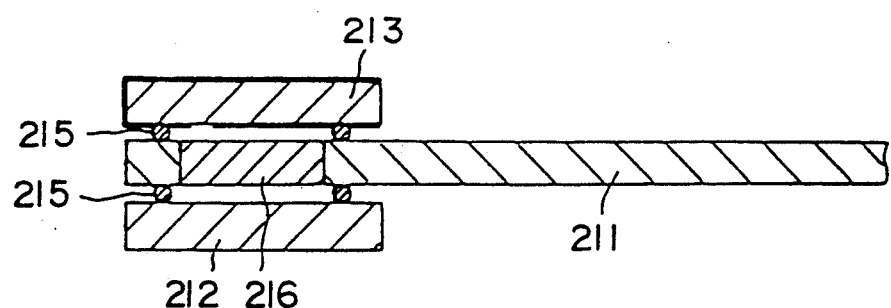

FIG_49A
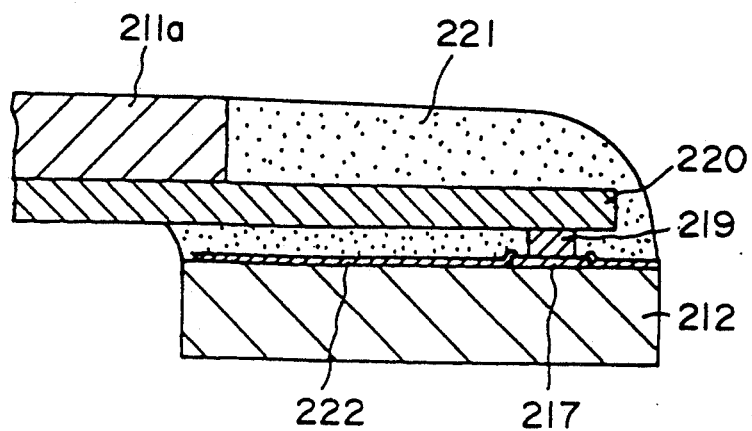
FIG_49B
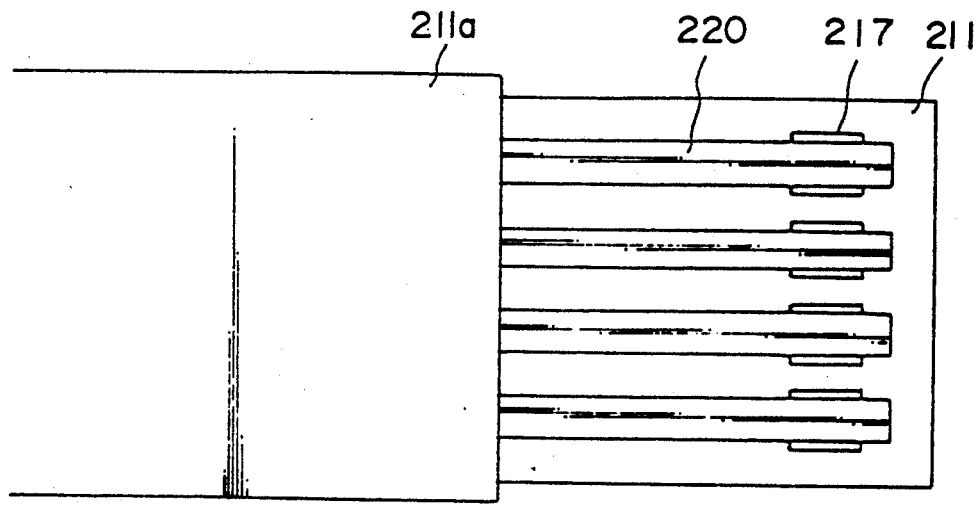

FIG._50
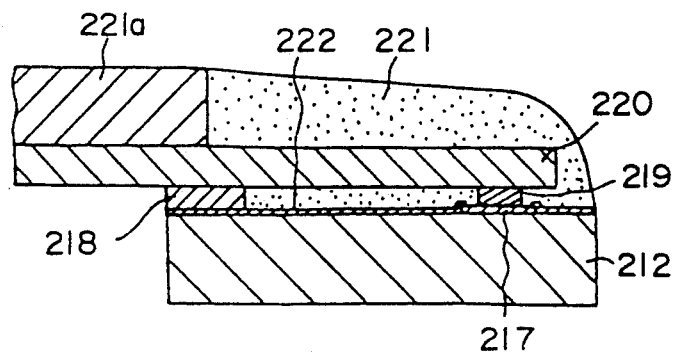
FIG._51A
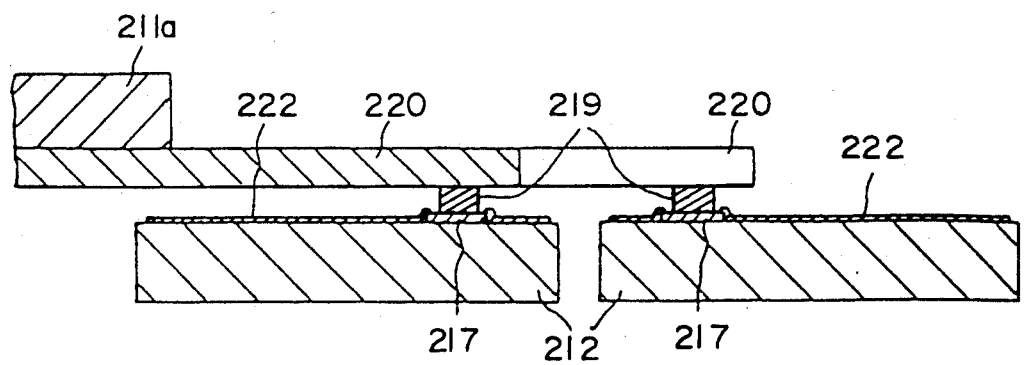
FIG._51B
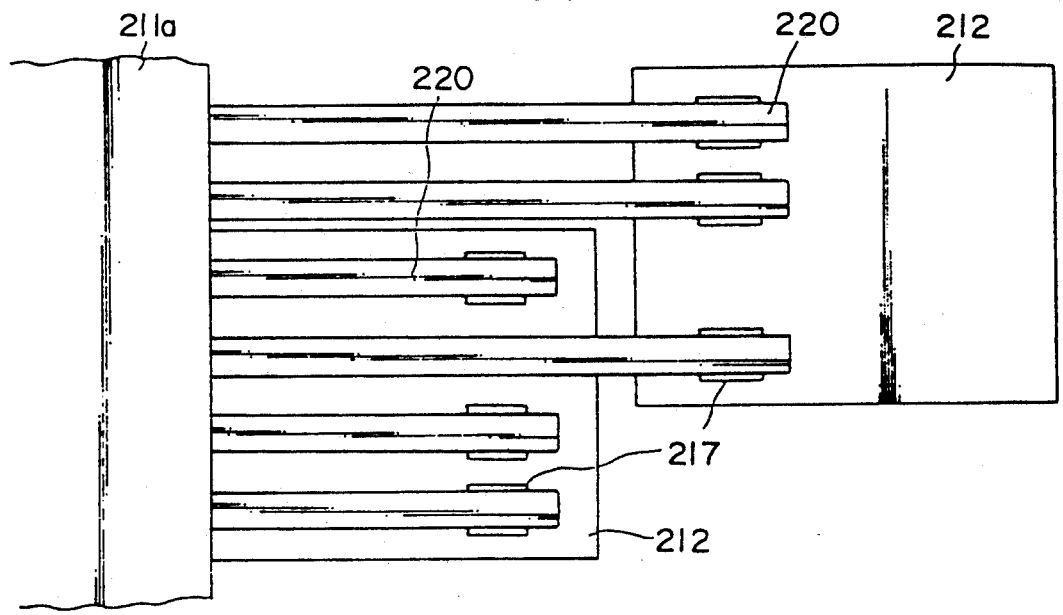

FIG_52A
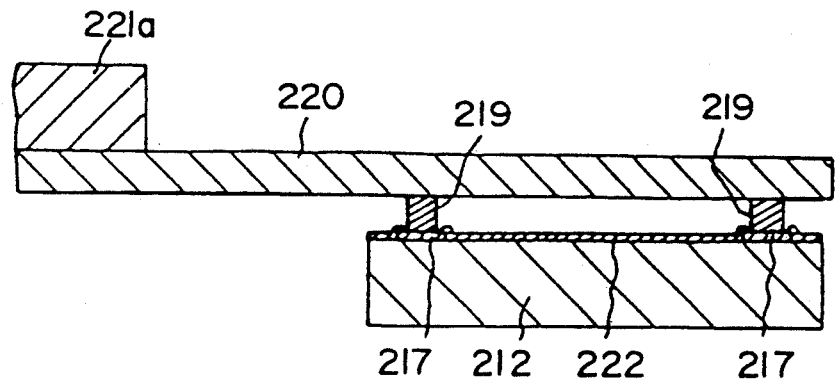
FIG_52B
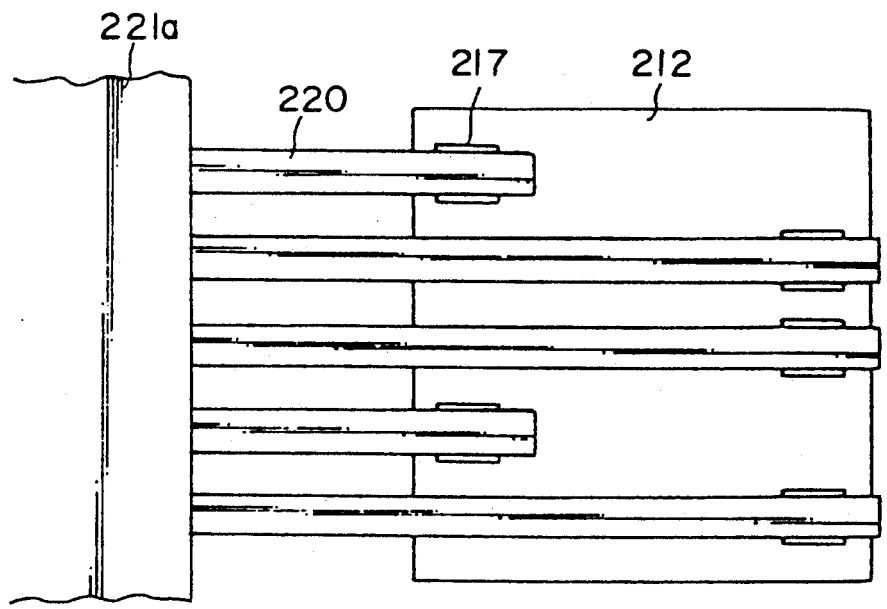

FIG_56
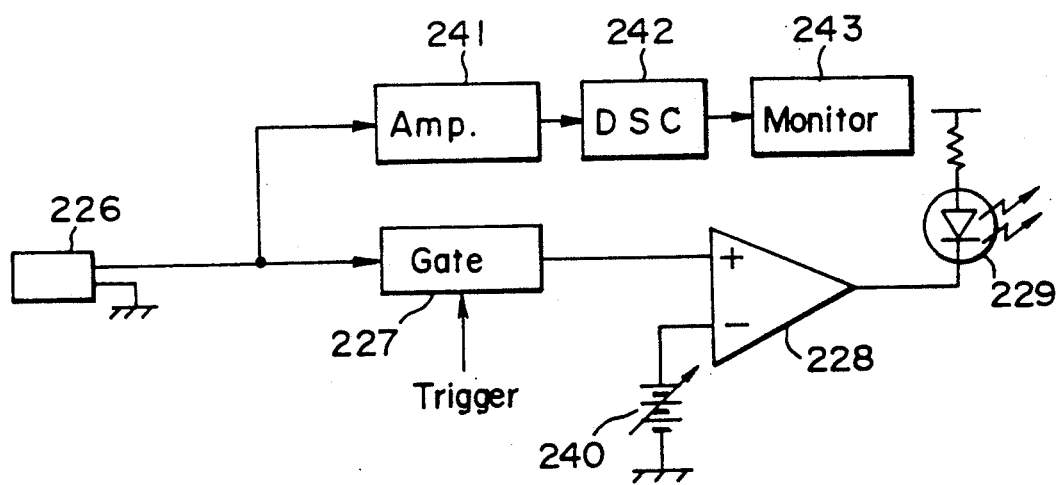

FIG_57
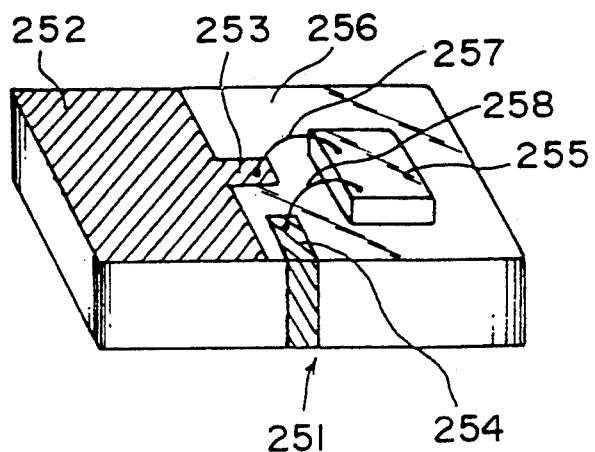
FIG_58
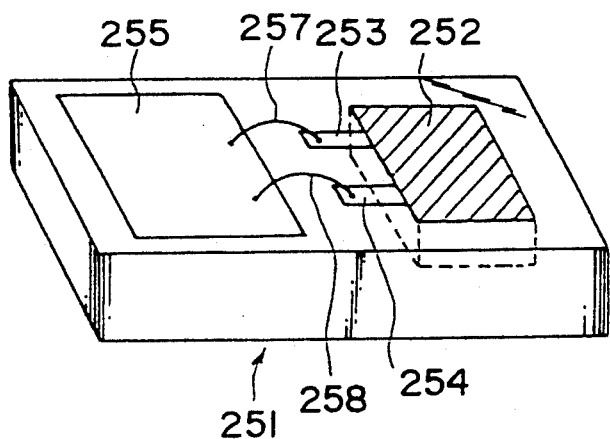

FIG_59
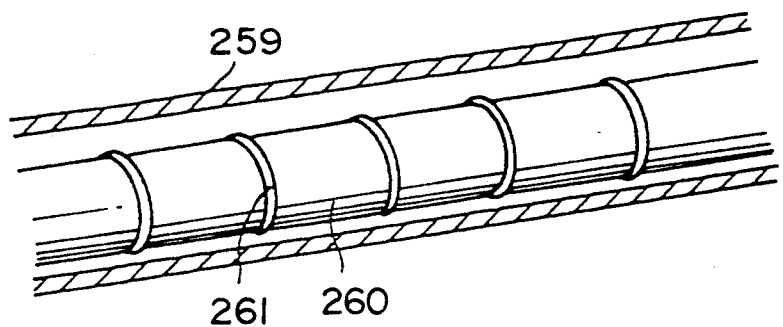
FIG_60
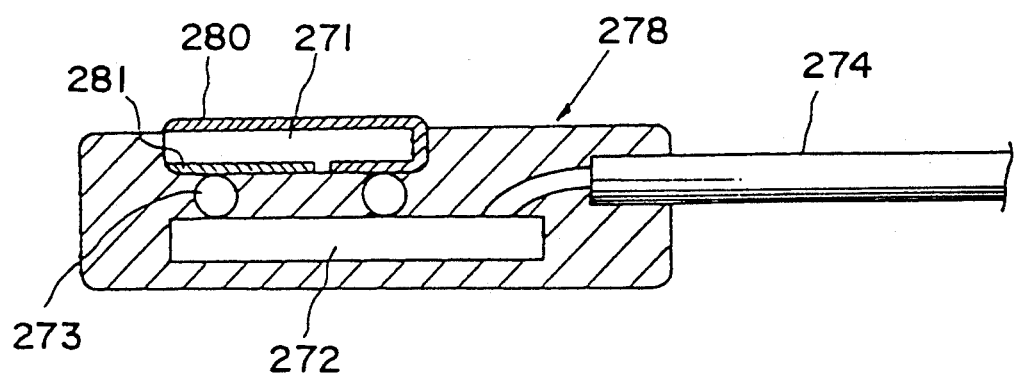

FIG_61A
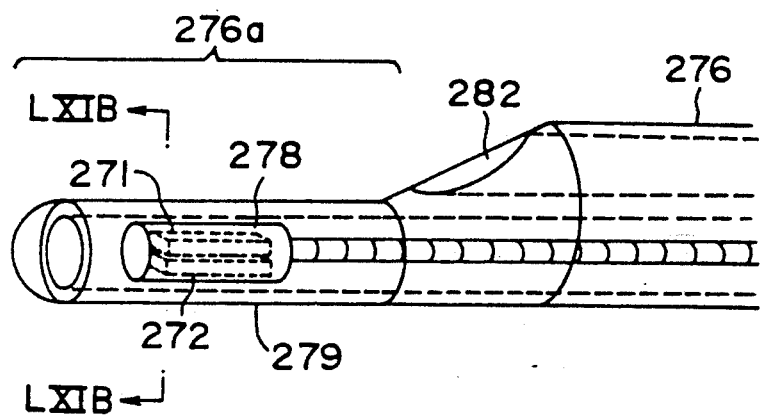
FIG_61B
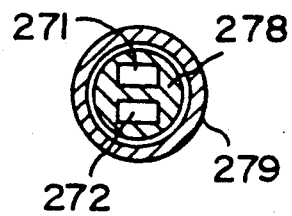

ULTRASONIC PROBE

BACKGROUND OF THE INVENTION

Field of the Invention and Related Art Statement

The present invention relates to an ultrasonic probe, and more particularly to an improvement of the ultrasonic probe for use in ultrasonic endoscope, ultrasonic diagnosing apparatus and other ultrasonic apparatuses.

There has been described a known ultrasonic probe in Japanese Utility Model Application Laid-open Publication Kokai Sho 60-45007.

FIG. 1 shows the known ultrasonic probe disclosed in said Publication. The ultrasonic probe comprises an ultrasonic vibrator 105 which includes a stack of piezoelectric vibrating element 105a, backing member 105b applied on a back side of the vibrating element and an acoustic matching layer 105c. The ultrasonic vibrator 105 is secured to a lower casing 102 which is provided at a tip of an upper casing 101. One lead wire 106a connected to an electrode applied on one surface of the piezoelectric element 105 is extended within an opening 104 formed in the lower casing 102 and the other lead wire 106b connected to an electrode applied on the other surface of the piezoelectric element 105 is extended along an outer surface of the lower casing 102. These lead wires 106a and 106b are further extended within the lower casing 102. Within the opening 104 is filled with a damper 107. Further the lower casing 102 is covered with a cap-like casing 103.

In the known ultrasonic probe mentioned above, the ultrasonic vibrator 105 and damper 107 are provided within the lower casing 102 when the lower casing is formed by molding. Then the cap-like casing 103 is also formed integrally with the lower casing 103 by molding.

FIG. 2 shows another known ultrasonic probe in which an ultrasonic vibrator 201 having lead wires connected to the electrodes is fixed within a casing 203 together with a damper 202 when the casing 203 is formed by molding. After that a resilient member 204 made of urethane rubber is secured to the casing.

In the known ultrasonic probe described in the Japanese Utility Model Application Publication Kokai Sho 60-45007, it is necessary to connect the lead conductors 106a and 106b to the electrodes of the ultrasonic vibrator 105. This results in that when the ultrasonic vibrator 105 is placed in a mold for forming the lower casing 102, the lead conductors might be cut, so that yield is liable to be low. Further it is practically difficult to provide a reference member for positioning the ultrasonic vibrator 105 within the mold, and therefore the ultrasonic vibrator is liable to be tilted or shifted.

The known ultrasonic probe illustrated in FIG. 2 has the same drawbacks as those mentioned above.

SUMMARY OF THE INVENTION

The present invention has for its object to provide a novel and useful ultrasonic probe which can overcome the above explained drawbacks of the known ultrasonic probes and can be manufactured easily at a low cost.

According to the invention an ultrasonic probe comprises

- an ultrasonic vibrator including a piezoelectric element and first and second electrodes applied on opposite main surfaces of the piezoelectric element for transmitting and receiving an ultrasonic wave;
- a supporting means for supporting the ultrasonic vibrator such that the ultrasonic wave generated by the ultrasonic vibrator is projected to an object under inspection and receiving the ultrasonic wave reflected by the object;
- a signal transmitting means provided integrally with the supporting means for transmitting a driving signal for the ultrasonic vibrator and an echo signal generated by the ultrasonic element; and
- a connecting means for connecting said signal transmitting means to the first and second electrodes of the ultrasonic vibrator.

In a preferred embodiment of the ultrasonic probe according to the invention, said supporting means comprises a housing made of electrically insulating material and having a recess for accommodating the ultrasonic vibrator and first and second connecting areas which are communicated with the recess and have a depth which is smaller than that of the recess. The ultrasonic vibrator is inserted into the recess such that portions of the first and second electrodes are exposed within the first and second connecting areas, respectively. Said signal transmitting means comprises first and second conductors and tips of these conductors are exposed within the first and second connecting areas, respectively. Said connecting means comprises first and second conductive members for connecting the tips of the first and second conductors to the first and second electrodes of the ultrasonic vibrator, respectively. The first and second conductive members are covered with an insulating layer.

BRIEF DESCRIPTION OF THE DRAWINGS

FIG. 1 is a cross sectional view showing an example of the known ultrasonic probe;

FIG. 2 is a cross sectional view illustrating another example of the known ultrasonic probe;

FIG. 3 is a cross sectional view depicting a principal construction of the ultrasonic probe according to the invention;

FIG. 4 is a cross sectional view showing an embodiment of the ultrasonic probe according to the invention;

FIG. 5 is a cross sectional view cut along a line X—X in FIG. 4;

FIG. 6 is a cross sectional view depicting the ultrasonic vibrator shown in FIG. 4;

FIG. 7, FIG. 8, FIG. 9 and FIG. 10 are cross sectional views showing first, second, third and fourth modifications of the first embodiment;

FIG. 11 is a cross sectional view illustrating a second embodiment of the ultrasonic probe according to the invention;

FIG. 12 is a cross sectional view showing a third embodiment of the ultrasonic probe according to the invention;

FIG. 13 is a cross sectional view depicting a fourth embodiment of the ultrasonic probe according to the invention;

FIG. 14 and FIG. 15 are cross sectional views representing first and second modifications of the housing shown in FIG. 11;

FIG. 16 is a cross sectional view showing a fifth embodiment of the ultrasonic probe according to the invention;

FIG. 17 is a cross sectional view cut along a line Y—Y in FIG. 16;

FIG. 18 is a cross sectional view illustrating a modification of the fifth embodiment shown in FIG. 16;

FIG. 19 is a cross sectional view showing a sixth embodiment of the ultrasonic probe according to the invention;

FIG. 20 and FIG. 21 are cross sectional views illustrating first and second modifications of the signal transmitting means shown in FIG. 19;

FIG. 22 is a cross sectional view depicting a seventh embodiment of the ultrasonic probe according to the invention;

FIG. 23 is a cross sectional view representing an eighth embodiment of the ultrasonic probe according to the invention;

FIG. 25 is an exploded perspective view depicting a mold for forming the ultrasonic probe;

FIG. 31, FIG. 32, FIG. 33 and FIG. 34 are schematic views illustrating second, third, fourth and fifth embodiments of the apparatus for forming the acoustic lens of the ultrasonic probe;

FIG. 35 is a cross sectional view showing the ultrasonic vibrator manufactured by the method illustrated in FIG. 34;

FIGS. 38A to 38D are cross sectional views representing successive steps for forming the acoustic matching layer and acoustic lens together with the ultrasonic vibrator;

FIG. 39 is a schematic view illustrating another embodiment of the method of manufacturing the acoustic matching layer and acoustic lens;

FIG. 40 is a cross sectional view showing the ultrasonic vibrator manufactured by the method represented in FIG. 39;

FIG. 41 is a schematic view showing still another embodiment of the method of manufacturing the acoustic matching layer and acoustic lens;

FIG. 42 is a cross sectional view showing a ninth embodiment of the ultrasonic probe according to the invention in which the connecting means comprises metal sponge or metal felt;

FIG. 43 is a cross sectional view illustrating a tenth embodiment of the ultrasonic probe according to the invention;

FIG. 44 is a cross sectional view depicting an eleventh embodiment of the ultrasonic probe according to the invention;

FIG. 45 is a perspective view showing the damping member shown in FIG. 44;

FIG. 46 is an enlarged cross sectional view representing a main portion of the ultrasonic probe shown in FIG. 44;

FIG. 47 is a cross sectional view showing a twelfth embodiment of the ultrasonic probe according to the invention in which the preamplifier is arranged near the ultrasonic vibrator;

FIG. 48 is a cross sectional view showing a thirteenth embodiment of the ultrasonic probe according to the invention;

FIGS. 49A and 49B are cross sectional and plan views, respectively illustrating a main portion of a fourteenth embodiment of the ultrasonic probe according to the invention;

FIG. 50 is a cross sectional view depicting a fifteenth embodiment of the ultrasonic probe according to the invention;

FIGS. 51A and 51B are cross sectional and plan views, respectively showing a sixteenth embodiment of the ultrasonic probe according to the invention;

FIGS. 52A and 52B are cross sectional and plan views, respectively illustrating a seventeenth embodiment of the ultrasonic probe according to the invention;

FIG. 56 is a block diagram showing a circuit for displaying the disconnection between the ultrasonic vibrator and the signal transmitting means;

FIG. 57 is a cross sectional view showing an eighteenth embodiment of the ultrasonic probe according to the invention in which the preamplifier is arranged integrally with the ultrasonic vibrator;

FIG. 58 is a perspective view illustrating a nineteenth embodiment of the ultrasonic probe according to the invention;

FIG. 59 is a perspective view showing the flexible shaft;

FIG. 60 is a cross sectional view depicting a twentieth embodiment of the ultrasonic probe according to the invention in which the ultrasonic vibrator and preamplifier are arranged near to each other; and FIG. 61A is a perspective view showing schematically the distal end of the insertion section in which the ultrasonic probe is inserted and FIG. 61B is a cross sectional view cut along a line A—A in FIG. 61A.

DESCRIPTION OF THE PREFERRED EMBODIMENTS

Figure 10:
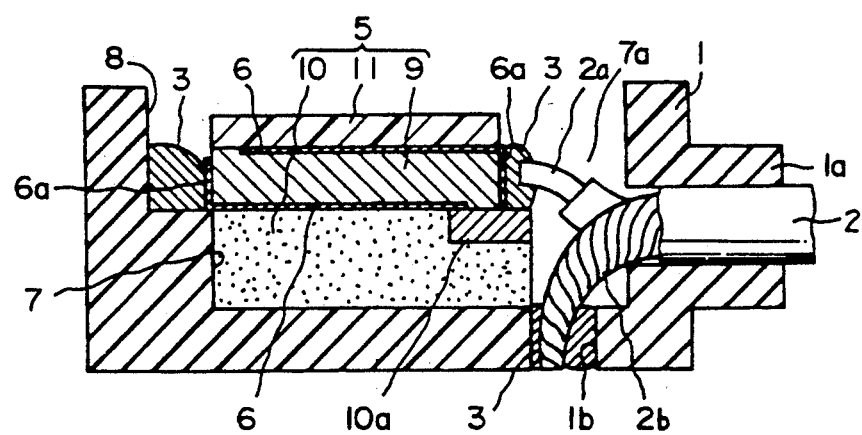

FIG. 3 is a cross sectional view showing a principal construction of the ultrasonic probe according to the invention. As illustrated in FIG. 3, a housing 1 includes a recess 7 for positioning an ultrasonic vibrator 5. The recess 7 is formed when the housing 1 is formed by molding. Further electric conductors 2 are embedded in the housing during the molding such that tips of the conductors are situated near electrodes 6 of the ultrasonic vibrator 5. The ultrasonic vibrator 5 is inserted into the recess 7 of the housing 1 made of electrically insulating material and is secured thereto with the aid of adhesive agent. The electrodes 6 of the ultrasonic vibrator 5 are connected to the tips of the conductors 2 by means of electrically conductive members 3. In order to isolate and shield the ultrasonic vibrator 5, conductors 2 and conductive members 3, there is provided an insulating member 4 on the conductive members.

The ultrasonic vibrator 5 comprises acoustic matching layer 11, piezoelectric element 9 and backing layer 10 which are placed one on the other in this order. Further the electrodes 6 are applied on respective main surfaces of the piezoelectric element 9.

FIGS. 4 to 6 illustrate a first embodiment of the ultrasonic probe according to the invention. When the ultrasonic probe is used together with the endoscope or is installed in the ultrasonic endoscope, it is inserted within a distal end of an insertion section of the endoscope. Therefore, the ultrasonic probe should be made very small. In FIG. 4 the ultrasonic probe is shown in a very large scale.

The basic construction of the present embodiment is substantially the same as the principal construction shown in FIG. 3, so that the detailed explanation thereof is omitted and portions similar to those shown in FIG. 3 are denoted by the same reference numerals used in FIG. 3. The housing 1 is formed by the molding of the insulating material and has a cylindrical shape. In the housing 1 there is formed the recess 7 having a relatively deep depth at the central position of the housing. In communication with the recess 7 there are formed connecting areas 8 having a shallow depth. The depth of the connecting areas 8 is substantially half of that of the recess 7. Within the housing the conductors 2 are embedded such that their tips are exposed within the connecting areas 8. The other ends of the conductors 2 are extended from one end surface of the cylindrical housing 1.

As shown in FIG. 6 the upper electrode 6 of the ultrasonic vibrator has an extended portion 6a which is placed on one side surface of the piezoelectric element 9 and similarly the lower electrode 6 also includes an extended portion 6a which is applied on the opposite side surface. The ultrasonic vibrator 5 is inserted into the recess 7 such that the extended portions 6a of the electrodes 6 are exposed within the connecting areas 8. The ultrasonic vibrator 5 is secured to the housing by means of adhesive agent 14 as illustrated in FIGS. 4 and 5.

The tips of the conductors 2 and the extended portions 6a of the electrodes 6 are electrically connected to each other by means of the conductive members 3 which are introduced into the connecting areas 8. The conductive members 3 in the connecting areas 8 are covered with the insulating members 4, so that all the conductive members are isolated. It should be noted that the ultrasonic vibrator 5 and insulating members 4 do not protrude from the surface of the housing 1.

The housing 1 may be made of any insulating material which can be molded. For instance, thermoplastic resin material such as phenol resin, furan resin, xylene formaldehyde resin, melamine resin, polyester resin and epoxy urea resin, thermoplastics such as polyethylene, polypropylene, polystyrene, polyacetatevinyl, polyacryrate, methacrylate resin, polyvinylchloride resin, fluorine-contained resin, polycarbonate resin and polyurethane resin, silicon rubber and mixtures of the above mentioned materials with fine particles of metal, ceramics, glass balloon, glass, resin and wood or paper fibers.

The conductive members 3 may be made of solder, conductive paste and conductive adhesive agent, and the insulating member 4 may be made of the same material as the housing, e.g. ceramics, glass, coating of resins and insulating paint.

In the following embodiments the housing 1, conductive members 3 and insulating members 4 may be made of the above mentioned materials.

When the ultrasonic probe of the first embodiment is used, a driving pulse voltage is applied to the ultrasonic vibrator 5 by means of the conductors 2 from a voltage source not shown and ultrasonic pulse is transmitted towards an object under inspection. The ultrasonic pulse is reflected by the object and the reflected ultrasonic wave is received by the ultrasonic vibrator 5 and is converted into an electric echo signal. The echo signal is then supplied to an ultrasonic image observing apparatus not shown.

In the present embodiment, since the signal transmitting conductors 2 are extended from the housing 1 at its one side surface, the conductors can be easily connected to lead wires. Further the ultrasonic vibrator 5 does not project beyond the housing surface, the ultrasonic vibrator can be effectively prevented from being injured.

FIGS. 7, 8 and 9 show modifications of the first embodiment of the ultrasonic probe according to the invention. In these modifications, there are formed pockets 12, 13 and 14 at an upper edge of the recess 7 of the housing 1 for retaining overflowed adhesive agent.

In the embodiment illustrated in FIG. 7, the pockets 12 are formed in the shape of steps, and in the embodiment shown in FIG. 8, the pockets 13 have inclined surfaces. In the embodiment of FIG. 9, the left hand pocket 12 has the same construction as that of the embodiment shown in FIG. 7. In this embodiment, the surface area of the backing member 10 is formed larger than the piezoelectric element 9 and acoustic matching layer 11 such that an edge of the piezoelectric element is separated from an edge of the backing member by a distance l. The right hand upper edge of the backing member 10 is cut off to form the pocket 15. The remaining construction of these modified embodiments is same as the first embodiment.

When the ultrasonic vibrator 5 is secured to the recess 7 of the housing 1, even if the adhesive agent 14 overflows from a space 16 between the inner surface of the recess 7 and the backing member 10, the overflowed adhesive agent is retained in the pockets 12, 13 and 14.

When the ultrasonic vibrator 5 is secured to the recess 7 of the housing 1, an air should not be introduced within the space 16 in order to make the firm connection. To this end it is advantageous to use an excessive amount of the adhesive agent. Then the adhesive agent overflows out of the space 16. The overflowed adhesive agent is liable to cover the extended portions 6a of the electrodes 6. This might deteriorate the conduction between the conductors 2 and the electrodes 6. The thickness t of the piezoelectric element 9 including the electrodes 6 and vibrating at about 15 MHz is about 150 μm, so that the extended portions 6a of the electrodes 6 are easily covered with the overflowed adhesive agent.

In the embodiments illustrated in FIGS. 7 to 9, the pockets 12, 13 and 14 can effectively serve to hold or retain the overflowed adhesive agent therein, so that exposed portions 6a of the electrodes 6 are hardly covered with the overflowed adhesive agent. As shown in FIG. 9, the pocket can be formed by cutting the edge of the backing member 10. Further it is advantageous to make larger the distance between the inner wall of the recess 7 and the extended portions 6a of the electrodes 6.

FIG. 10 shows another modification of the first embodiment. In this modified embodiment, the housing is formed by electrically conductive material and one of the signal transmitting conductors is connected to the housing.

A housing 1 shown in FIG. 10 is made of metal and has a wire supporting portion 1a. In the housing the relatively large recess 7 and the connecting area 8 are formed. The depth of the connecting area 8 is smaller than the recess 7.

The ultrasonic vibrator 5 including the piezoelectric element 9 having the electrodes 6 with the extended portions 6a, backing member 10 and acoustic matching layer 11 is placed in the recess 7 such that the extended portion 6a of the lower electrode 6 is exposed within the connecting area 8. It should be noted that the extended portion 6a of the upper electrode 6 is exposed within a space 7a of the recess 7. In the backing member 10 there is provided an insulating member 10a at a position at which the lower electrode and the extended portion 6a of the upper electrode are in contact with the backing member 10. In this manner the upper and lower electrodes 6 can be isolated from each other.

In the present embodiment, the signal transmitting means 2 comprises a coaxial cable. The front end of the coaxial cable 2 is inserted into a hole formed in the wire supporting portion 1a and is extended into the space 7a. One conductor 2a of the coaxial cable 2 is directly connected to the extended portion 6a of the upper electrode 6 and the other conductor 2b is inserted into a hole 1b formed in the bottom of the housing 1 and is electrically connected thereto by means of the conductive member 3. Into the connecting area 8 formed in the housing 1 is inserted the conductive member 3 to connect the housing 1 to the extended portion 6a of the lower electrode 6. In this manner the conductor, i.e. a shielding wire 2b of the coaxial cable 2 is electrically connected to the lower electrode 6 by means of the conductive member 3 provided in the hole 1b, conductive housing 1, conductive member 3 provided in the connecting area 8 and the extended portion 6a of the lower electrode.

In the present embodiment, one of the conductors of coaxial cable 2 does not pass under the backing member 10 of the ultrasonic probe, so that the thickness of the housing 1 can be reduced and the whole ultrasonic probe can be made small. Further since the housing 1 is made of a conductive material such as metal, the ultrasonic vibrator 5 can be effectively protected against external noise. Further, as illustrated in FIG. 10, the electrical connection of the lower electrode 6 of the ultrasonic vibrator 5 to the shielding conductor 2b of the coaxial cable 2 is achieved merely by connecting extended portion 6a of the lower electrode to the housing 1 by dropping the conductive member 3 into the connecting area 8, inserting the shielding conductor 2b into the hole 1b formed in the housing 1 and securing the shielding conductor 2b to the hole 1b by the conductive member 3. Therefore, it is no longer necessary to extend the shielding conductor 2b up to the portion 6a of the lower electrode 6 and thus the ultrasonic probe can be manufactured easily and efficiently. Moreover, since backing member 10 includes the insulating member 10a at a position at which the extended portion 6a of the upper electrode 6 is brought into contact with the backing member 10, the remaining portion of the backing member 10 may be electrically conductive.

FIG. 11 is a cross sectional view showing a second embodiment of the ultrasonic probe according to the invention. In this embodiment, a housing 1A is made of a material including fine particles of sound absorbing material and the housing serves as the backing member. In this case the recess 7A formed in the housing 1A can have the same depth as the connecting areas 8. Therefore, the recess 7A and connecting areas 8 can be easily formed by the molding. Further, in this embodiment, the thickness of a portion of the housing 1A which serves as the backing member has a larger depth H, so that the property of the ultrasonic vibrator 5 can be improved. Moreover, the step of providing the backing member can be dispensed with.

FIG. 12 is a cross sectional view illustrating a third embodiment of the ultrasonic probe according to the invention. In the present embodiment, the signal transmitting means comprises a coaxial cable 19 which is embedded in the housing 1.

A core conductor 17 of the coaxial cable 19 and an outer shielding conductor 18 are separated within the housing 1 and tips of these conductors are exposed within the connecting areas 8. In order to decrease the tension applied to the coaxial cable 19 at a portion where the coaxial cable is extended out of the housing 1, there is formed a tapered projection 21 whose cross sectional area becomes smaller toward outside. The remaining construction is the same as the first embodiment.

In the third embodiment shown in FIG. 12, the electrodes of the ultrasonic vibrator 5 can be directly connected to an amplifier 20 by means of the coaxial cable 19. Therefore, the signal transmitting means comprises only one coaxial cable 19, and thus the cost of the ultrasonic probe can be reduced. Further, the number of manufacturing steps can be reduced and the manufacturing cost can be reduced, because the connection between the conductors and lead wires is not required. Moreover the mechanical strength is increased by the tapered projection 21, and thus the ultrasonic probe can be used in a severer condition.

FIG. 13 is a perspective view showing a fourth embodiment of the ultrasonic probe according to the invention. In this fourth embodiment, the signal transmitting means comprises a flexible print circuit board 22. For the sake of simplicity the flexible print circuit board is called FPC. A connecting area 8A is formed by cutting a portion of the housing 1B having the cylindrical shape. In the center of the flat surface of the housing there is formed a recess 7. In the recess 7 the ultrasonic vibrator 5 is inserted and is secured thereto by the adhesive agent. In FPC 22 there is formed a rectangular opening 22a which corresponds to the recess 7. On FPC 22 there are formed conductive patterns 22b and 22c. FPC 22 is placed on the flat surface of the housing 1B such that the ultrasonic vibrator 5 is projected through the opening 22a and the conductive patterns 22b and 22c are situated near the extended portions 6a of the electrodes 6 of the ultrasonic vibrator 5. Then the conductive patterns 22b and 22c are connected to the extended portions 6a by means of conductive members 3. Finally the conductive patterns 22b and 22c and conductive members 3 are covered with a insulating layer not shown. The remaining construction is same as the first embodiment.

In the fourth embodiment, the signal transmitting means comprises FPC 22 and the signal is transmitted by means of FPC.

It should be noted that in the fourth embodiment, the signal transmitting means is consisting of the flexible print circuit board, but the conductive patterns may be directly applied on the housing by deposition, plating, painting and printing.

FIGS. 14 and 15 are cross sectional views illustrating modifications of the fourth embodiment.

In the first modified embodiment shown in FIG. 14, the front end of a housing 1C is formed in a frustoconical shape. When the ultrasonic probe having the housing whose front end is shaped frustoconically is inserted into a tube 23 of an insertion section, the resistance is decreased, so that the ultrasonic probe can be inserted easily. Further the ultrasonic probe within the tube 23 can be easily rotated by an actuator not shown, and thus the ultrasonic probe can be rotated at a given constant scanning speed and undesired wow is reduced. Therefore, accurate ultrasonic images can be obtained. It should be noted that the shape of the front end of the housing is not limited to the frustoconical shape, but may be formed in any other shape which can reduce the frictional and sliding resistances. For instance, the front end of the housing may be formed into conical shape, pyramid shape or spindle shape.

In the second modified embodiment illustrated in FIG. 15, in the front end of a housing 1D there is formed a female screw hole 24, and a male screw 26 having a substantially semi-spherical top 25 is secured to the female screw hole 24. It is possible to carry up to the distal end of the tube a grease back, needle or permanent magnet by securing them to the front end of the housing 1D instead of the semi-spherical top 25.

FIGS. 16 and 17 are cross sectional views showing a fifth embodiment of the ultrasonic probe according to the invention. In the present embodiment, the acoustic matching layer 11 shown in FIGS. 4, 10 and 11 is formed by the insulating layer which covers the conductive members 3. That is to say, the signal transmitting conductors 2 are connected to the extended portions 6a of electrodes 6 of the ultrasonic vibrator 5 by means of the conductive members 3 and the conductive members are covered with the insulating layer 4. In the present embodiment, the acoustic matching layer of the ultrasonic vibrator 5 is formed by the above mentioned insulating layer 4.

The insulating layer 4 is extended over the front surface of the ultrasonic vibrator 5 and an acoustic matching layer 27 is formed by the insulating layer having a thickness $H_1$ (see FIG. 17).

In the present embodiment, it is no more necessary to provide the acoustic matching layer, so that the manufacturing process can be made much simpler and the cost of the ultrasonic probe can be reduced.

FIG. 18 shows a modification of the fifth embodiment shown in FIGS. 16 and 17. In this modified embodiment, the surface of the insulating layer 4 is curved to form an acoustic lens 27A. It should be noted that when the curvature of the curved surface of the insulating layer 4 is made coincided with the curvature of the housing 1, the manufacturing can be further made simple.

FIG. 19 is a cross sectional view illustrating a sixth embodiment of the ultrasonic probe according to the invention. In this embodiment, a connector 28 of the signal transmitting means is provided at one side of the housing integrally therewith and the transmission of the signal can be realized simply.

One of the conductors 2 is projected from the side wall of the housing 1 as a center conductor 28a and the other conductor is connected to a conductive tube 28b which is arranged around the center conductor 28a.

The connector 28 is integrally formed with the housing 1 during the molding. In an outer surface of a portion of the housing 1 which is near the connector 28 there is formed a female screw thread 29. Further at a projection 30 which is communicated with said portion of the housing there is arranged an 0-ring 31 for preventing the intrusion of water. The remaining construction is same as that of the embodiment illustrated in FIG. 14.

There is further provided a connector 32 which is detachably coupled with the connector 28. The connector 32 comprises an inner conductive tube 33 into which the center conductor 28a of the connector 28 is inserted and an outer conductive tube 34 into which the conductive tube 28b of the connector 28 is inserted. To the conductive tubes 33 and 34 are connected lead wires by soldering. The connecting portions of the conductive tubes 33 and 34 and the lead wires are embedded in a receptacle 35 made of insulating material. The receptacle 35 has a step 35a and a shoulder 36 which receives the projection 30 of the housing 1. The receptacle 35 is surrounded by a sleeve 37 which has a female screw thread 38 which is coupled with the male thread 29 formed in the housing 1.

In the sixth embodiment, when the sleeve 37 is screwed to the housing 1, the connector 32 is moved toward the connector 28 and these connectors are coupled with each other firmly.

In the present embodiment, when the ultrasonic probe is broken, the ultrasonic probe can be easily replaced by disconnecting the connectors 28 and 32. Further a plurality of ultrasonic probes having different operating frequencies can be selectively used, so that the inspection can be extended.

It should be noted that the present invention is not limited to the above explained coupling means, but any other coupling means may be utilized. For instance the relative rotation of the connectors may be attained by providing a pin and a hole. Further the connectors may be coupled in a single action by utilizing a spring member.

FIGS. 20 and 21 are cross sectional view showing two modifications of the embodiment shown in FIG. 19.

In the first modification, the conductors 2 of the signal transmitting means are projected from one side surface of the housing 1 by different lengths up to end portions 2A and 2B. Further in the conductors 2 there are formed thin portions 2Aa and 2Ba which constitute click mechanisms. An external connector 40 comprises receptacles 41A and 41B for receiving the end portions 2A and 2B, respectively. The receptacles 41A and 41B are formed by resilient leaf springs and include projections 41Aa and 41Ba which are clamped into the thin portions 41Aa and 41Ba of the conductors 2.

In this modification, the connector formed by the conductive pins 2A and 2B and the connector formed by the resilient receptacles 41A and 41B can be coupled with each other electrically and mechanically, so that the construction is simple and the connecting and disconnecting operations can be performed easily. Further the connectors can be manufactured at a very low cost.

In the second modification depicted in FIG. 21, the signal transmitting means includes the coaxial cable 19 similar to the third embodiment(see FIG. 12) and the rotating force transferring means is arranged around the coaxial cable.

The core conductor 17 of the coaxial cable 19 is connected to the upper electrode by means of the conductive member 3 and the shield conductor 18 is connected to the lower electrode with the aid of the conductive member 3. To the right hand end of the housing 1 is secured a flexible shaft 42 formed by double coils and the coaxial cable 19 is passed through the shaft. The other end of the flexible shaft 42 is connected to a driving means for rotating the ultrasonic probe.

The driving means comprises a motor 43, a gear 44 coupled with an output shaft of the motor and a gear 45 which is secured to the end of the flexible shaft 42 and is engaged with the gear 44. The coaxial cable 19 passed through the flexible shaft 42 is connected to an amplifier 20 by means of a rotary connector 46.

In the modification shown in FIG. 21, the rotation of the motor 43 is transferred to the ultrasonic probe by means of the flexible shaft 42 and the ultrasonic vibrator 5 is rotated to effect the ultrasonic scan. The echo signal generated by the ultrasonic vibrator 5 is supplied to the amplifier 20 by means of the coaxial cable 19 and rotary connector 46. In this manner the mechanical radial scan can be effected.

In the present embodiment, the flexible shaft 42 is connected to the housing 1 when the housing is formed by molding, so that the connecting operation can be dispensed with, and thus the manufacturing cost can be reduced. Further the integral molding can increase the mechanical strength of the connection and thus the ultrasonic probe can be used for a long time. Moreover the flexible shaft 42 also serves to protect the coaxial cable 19.

FIG. 22 is a cross section depicting a seventh embodiment of the ultrasonic probe according to the invention. In this embodiment, a coil 47 for effecting the impedance matching between the ultrasonic vibrator 5 and the external circuit is provided within the ultrasonic probe.

In the right hand portion of the housing 1 there is formed a thin portion 1a and the impedance matching coil 47 is wound around the thin portion. Terminals 47a and 47b of the coil 49 are connected to the tips of the conductors 2 by means of the conductive members 3 together with the extended portions of the electrodes. The conductive portions and coil 47 are covered with the insulating member 4. The remaining construction of the present embodiment is similar to the first embodiment (see FIG. 4).

In the seventh embodiment explained above the coil 47 provided on the thin portion 1a of the housing 1 can take the impedance matching between the ultrasonic vibrator 5 and the external circuit not shown, so that the property of the ultrasonic probe is improved.

Further the coil 47 is wound around the thin portion 1a of the housing after the signal transmitting wires are connected to the electrodes, and thus the winding operation becomes easy and the number of turns of the coil can be adjusted at will. Moreover, since the coil 47 is provided on the housing 1, the whole construction of the ultrasonic probe can be made still small.

FIG. 23 is a cross sectional view illustrating an eighth embodiment of the ultrasonic probe according to the invention. Also in the present embodiment, the impedance matching element is provided in the housing. That is to say, an inductance element 48 is provided within a mold for forming the housing 1 and is electrically connected to the conductors 2 by means of wires 49. After that the insulating material is introduced into the mold to form the housing 1.

In the present embodiment, since it is no more necessary to wind the matching coil 47, the manufacturing cost can be further reduced as compared with the seventh embodiment.

In the seventh and eighth embodiments, the impedance matching coil is connected in parallel with the ultrasonic vibrator 5, but it may be arranged in series with the ultrasonic vibrator. Further instead of the impedance matching element an IC tip including the transmitting and receiving circuits may be arranged within the housing. In such a case it is necessary to provide power source lines in addition to the signal transmitting lines.

Now the method of manufacturing the above mentioned first embodiment of the ultrasonic probe according to the invention will be explained with reference to FIGS. 24 to 29.

FIG. 25 is an exploded perspective view showing a mold for manufacturing the housing 1. The mold comprises first and second mold halves 50A and 50B, first and second conductor receiving members 51A and 51B, intermediate plate 52 and resin pot 53.

Figure 26:
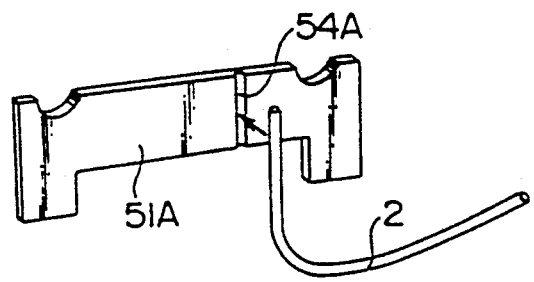
FIG. 26 is a perspective view showing a receptacle for a conductor clamped into the mold.
Figure 27:
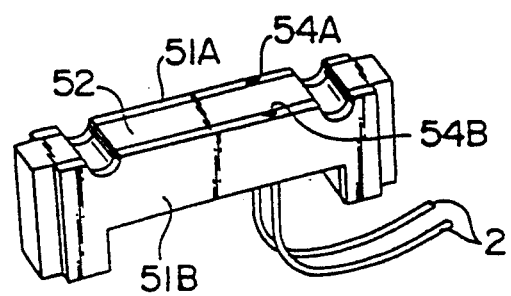
FIG. 27 is perspective view representing the condition of supporting the conductor with the aid of the receptacle shown in FIG. 26.
Figure 28:
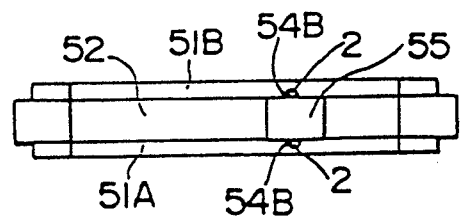
FIG. 28 is a bottom view of the receptacle shown in FIG. 27.
Figure 29:
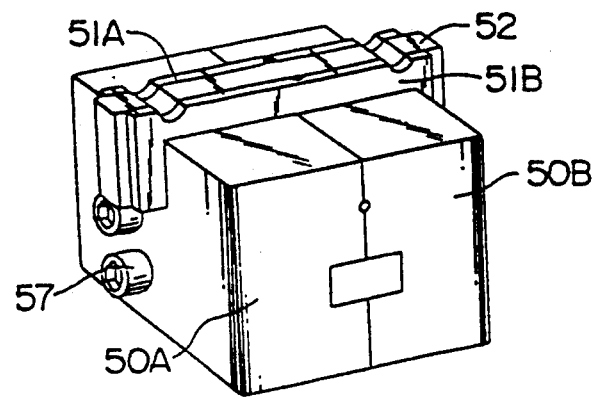
FIG. 29 is a perspective view illustrating the mold in which the conductor receptacle has been set.

The first and second conductor receiving members 51A and 51B are used to support the two conductors 2 of the signal transmitting means in given positions in the mold. That is to say, the conductors are clamped into the first and second conductor receiving members 51A and 51B and then these members are arranged in the molding space defined by the first and second mold halves 50A and 50B. The first and second conductor receiving members 51A and 51B have the same configuration and size and are formed by plate-like members having the inverted channel shape. FIG. 26 shows the first conductor receiving member 51A. In the inner surfaces of the members 51A and 51B there are formed grooves 54A and 54B for accommodating the conductors 2. By interposing the intermediate plate 52 between the first and second conductor receiving members 51A and 51B as illustrated in FIG. 27, the conductors 2 can be held in position. FIG. 28 is a bottom view of the assembly of the first and second conductor receiving members 51A and 51B and intermediate plate 52. In the lower surface of the intermediate plate 52 there is formed a rectangular projection 55 which serves to form the recess 7. The assembly of the members 51A and 51B and intermediate plate 52 is then place in the molding space formed by the first and second mold halves 50A and 50B which are coupled with each other by means of bolts 56 and 57 as illustrated in FIG. 29. In this manner the conductors 2 are arranged in position within the mold.

The molding space for forming the housing is defined by separated recesses 50Aa and 50Ba (in FIG. 25 the recess 50Aa is not shown) formed in the first and second mold halves 50A and 50B, respectively. Into the separated recesses 50Aa and 50Ba molding material is injected by means of the resin pot 53.

FIGS. 24A to 24D show successive steps for manufacturing the ultrasonic probe by using the above mentioned mold. In a first step depicted in FIG. 24A, the housing 1 is formed by injecting the molding material into the separated recesses 50Aa and 50Ba by means of the resin pot 53. In this case the molding resin material can be injected into the mold efficiently by utilizing the vacuum. Further it is also advantageous to apply a mold separating agent on the inner surfaces of the recesses 50Aa and 50Ba for promoting the separation of the housing from the mold. After the injected resin has been hardened, the housing 1 is removed from the mold. Then the housing 1 is washed to remove the mold separating agent. In this manner the housing 1 in which the conductors 2 are embedded can be obtained.

Figure 24A:
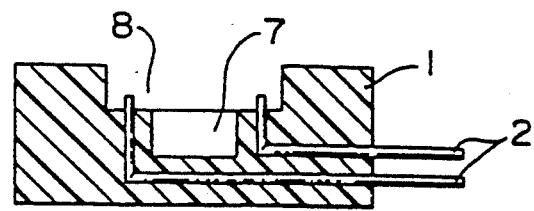
FIGS. 24A to 24D are cross sectional views showing successive steps for manufacturing the ultrasonic probe illustrated in FIG. 11.
Figure 24B:
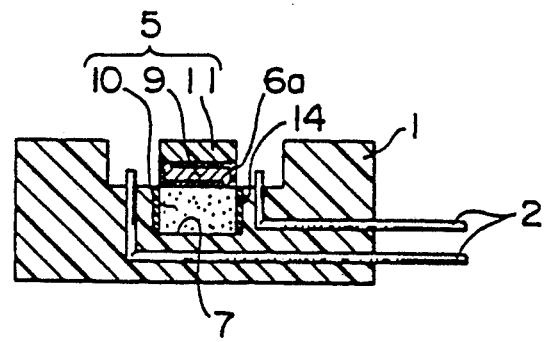

In the second step shown in FIG. 24B, the ultrasonic vibrator 5 formed by stacking the piezoelectric element 9 having the upper and lower electrodes 6, backing layer 10 and acoustic matching layer 11 is inserted into the recess 7 formed in the housing 1 and is secured thereto by means of the adhesive agent 14. In order to avoid that the adhesive agent 14 is not applied on the extended portions 6a of the electrodes 6, it is advantageous to form the portions for retaining the overflowed adhesive agent as in the embodiments illustrated in FIGS. 7, 8 and 9.

Figure 24C:
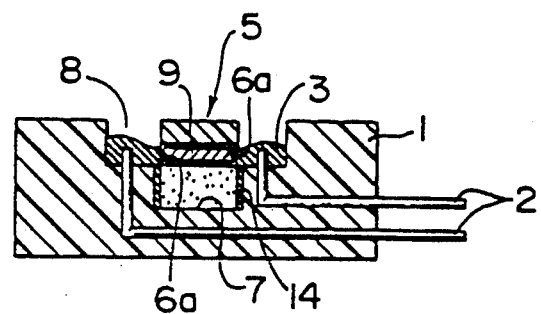

In the third step shown in FIG. 24C, the tips of the conductors 2 are electrically connected to the extended portions 6a of the electrodes 6 by means of the conductive members 3.

Figure 24D:
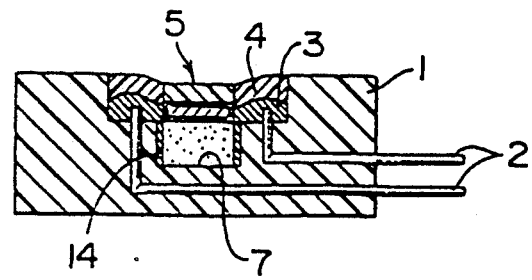

In the fourth step shown in FIG. 24D, the insulating layer 4 is applied except for the surface of the ultrasonic vibrator 5.

It should be noted that in each steps the hardening of the resin may be promoted by effecting the heating process.

In the ultrasonic probe according to the invention, the housing having the conductors embedded therein is first formed, then the ultrasonic vibrator is secured to the housing, the conductors are connected to the electrodes and finally the insulating process is performed to isolate the electrodes and conductors from the external.

By means of the method of manufacturing the ultrasonic probe explained above, the outer configuration of the ultrasonic probe can be determined at will and the manufacturing steps become simple, so that any experienced worker is not required. In this manner the ultrasonic probe can be manufactured stably at a low cost. Particularly the ultrasonic probe having a very small dimension can be manufactured.

As explained above according to the present invention, the signal transmitting means and the housing are formed integrally with each other and then the ultrasonic probe is arranged on the housing and the electrodes are connected to the conductors. Therefore, the ultrasonic probe having any desired outer configuration can be manufactured simply.

In the ultrasonic vibrator, the piezoelectric element is driven to generate the ultrasonic wave and the ultrasonic wave reflected by the object under inspection is received. In order to increase the efficiency of the ultrasonic wave transmission and reception it has been well known to provide an acoustic convex or concave lens. In the known ultrasonic probe, such an acoustic lens is formed by injecting suitable material into a mold.

For instance, in Japanese Utility Model Application Publication Kokai Sho 51-51181, a silicon rubber convex lens is formed with the aid of the mold and then the lens is secured on the surface of the ultrasonic vibrator.

In the known method explained above, the number of manufacturing steps is large and the ultrasonic vibrator having good property could not be obtained due to the fact unevenness in the thickness of the adhesive layer for securing the lens on the vibrator and the shift of the optical axis of the lens when the lens is fixed to the vibrator. Further when the molded lens is removed from the mold, the lens is liable to be broken and deformed because the lens is very small and could not be easily taken off the mold. This results in the decrease in the manufacturing yield. Moreover it is very difficult to apply the small lens on the vibrator.

The present invention has for its object to overcome the above mentioned drawbacks of the known ultrasonic probe and to provide a novel and useful ultrasonic vibrator in which the acoustic lens can be manufactured easily and accurately.

Figure 30:
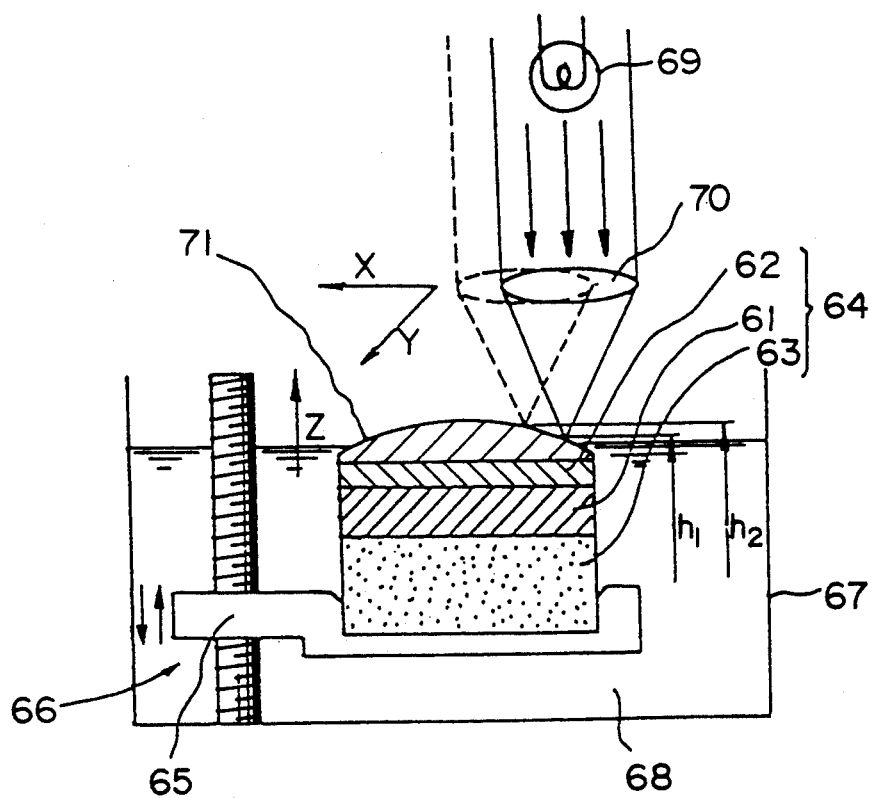
FIG. 30 is a schematic view showing a first embodiment of the apparatus for forming the acoustic lens of the ultrasonic probe.

FIG. 30 is a schematic view showing the method of manufacturing the acoustic lens for use in the ultrasonic probe according to the invention. The assembly of a piezoelectric element 61, acoustic matching layer 62 and damping layer, i.e. backing layer 63 is placed on an arm 65 of a position adjusting device 66. Then the assembly is immersed into a solution 68 of resin which is hardened under the exposure of ultraviolet contained in a vessel 67. Hereinafter such a resin is called ultraviolet setting resin. The ultrasonic vibrator is placed on the arm 65 such that the matching layer 61 is faced upwards. The ultraviolet setting resin is commercially available under the trade name "KR-400" manufactured and sold by ASAHI DENKA COMPANY. It should be noted that any other material having the same property may be equally used.

Above the vessel 67 containing the ultraviolet setting resin there is arranged an ultraviolet light source 69 and a lens 70 for focussing the ultraviolet ray emitted from the UV light source onto the surface of the ultraviolet setting resin 68. The UV light source 69 and lens 70 are arranged movably in X and Y directions by means of a suitable driving device not shown.

At first the arm 65 is driven such that the surface of the matching layer 61 is situated just below the liquid level of the ultraviolet setting resin 68 and the ultraviolet ray is focused on the liquid surface. Therefore, a thin layer of the ultraviolet resin is formed on the matching layer 61. By repeating the above mentioned process while the arm 65 is moved in Z direction as shown by $h_1$ and $h_2$ and the UV light source 69 and lens 70 are moved in the X-Y plane, it is possible to form an acoustic lens 71.

In the manner explained above it is possible to form the acoustic lens 71 on the acoustic matching layer 61 integrally therewith. Since the separately formed acoustic lens is not secured on the matching layer, the manufacturing efficiency can be increased. Further the acoustic lens 71 is formed in the liquid, air bubbles are hardly introduced therein and the property of the acoustic lens can be improved. It should be noted that the control in the X, Y and Z directions can be carried out by any desired method such as the computer control.

Figure 31:
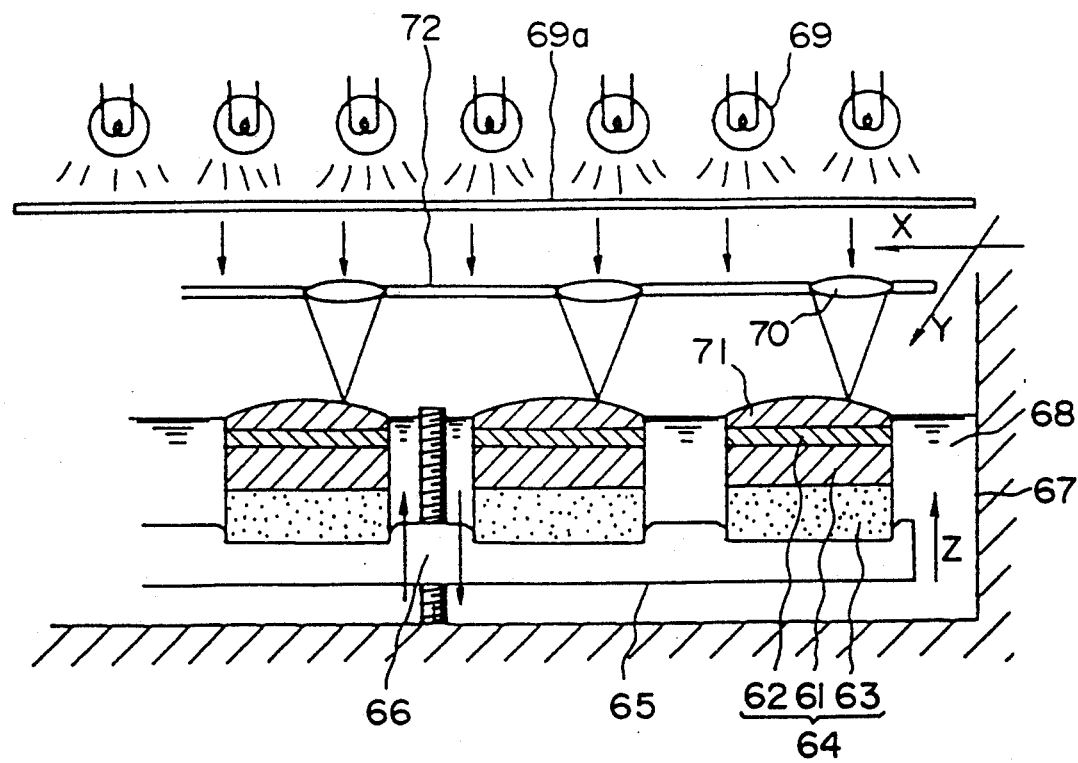

FIG. 31 shows a second embodiment of the method of manufacturing the acoustic lens. In this embodiment portions similar to those shown in FIG. 30 are denoted by the same reference numerals used in FIG. 30. In the present embodiment a plurality of acoustic lenses can be manufactured simultaneously.

A plurality of ultrasonic vibrators 64 are placed equidistantly on the arm 65 of the position adjusting device 66. Above the vessel 67 containing the ultraviolet setting resin liquid 68 are arranged a plurality of UV light sources 69 at positions corresponding to the ultrasonic vibrators 64. Under the UV light sources 69 there is arranged a diffusion plate 69a for diffusing the ultraviolet ray. Below the diffusion plate 69a are arranged a plurality of lenses 70 secured to a lens holder 72. The lens holder 72 is moved in the X and Y directions by means of the driving means. The lens holder 72 is made of material which does not pass the ultraviolet ray, so that the ultraviolet ray is made incident upon the ultraviolet setting resin liquid only by means of the lenses 70.

At first the height adjusting device 65 and lens holder moving device are set such that ultraviolet light beams are focused on the surface of the ultraviolet setting resin liquid 68 at given positions on the matching layers 62. Then the UV light sources 69 are energized to form thin layers of the ultraviolet setting resin layers on the matching layers. During the exposure the driving devices are controlled to move the ultrasonic vibrators 64 and the lenses 70 to form the acoustic lenses 71 on the matching layers 62 simultaneously.

Figure 32:
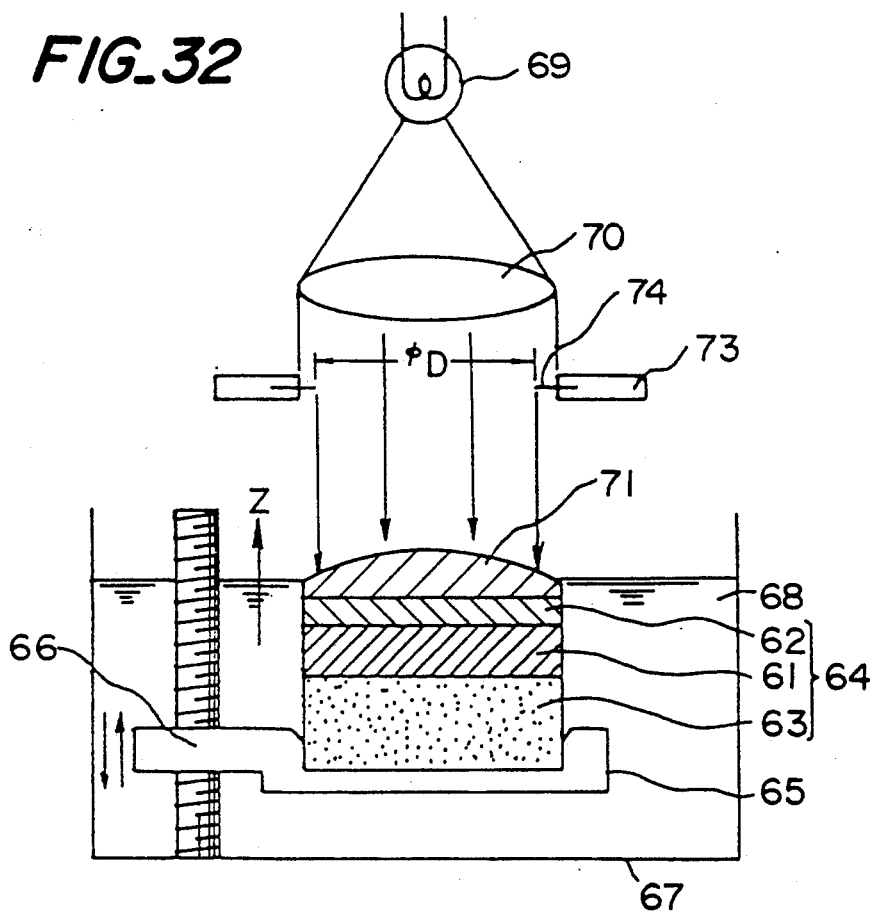

FIG. 32 illustrates still another embodiment of the method of forming the acoustic lens integrally with the matching layer of the ultrasonic vibrator. In the present embodiment, below the lens 70 is arranged a stop 73 having movable vanes 74. The stop 73 is moved together with the UV light sources 69 and lens 70 in the X and Y directions. The remaining construction is same as the first embodiment shown in FIG. 30. In the present embodiment, the optical axis of the UV light source 69, lens 70 and stop 73 is first aligned with an optical axis of an acoustic lens to be formed. In this case, the UV light source 69 is positioned at a focal point of the lens 70 so that the light flux emanating from the lens becomes a parallel light beam.

Then the height adjusting device 66 is controlled such that the surface of the matching layer 62 of the ultrasonic vibrator 64 is aligned with the liquid level. At the same time the stop 73 is controlled to adjust an aperture diameter $\phi_D$ which is defined by the vanes 74. In this manner the ultraviolet setting resin on the matching layer 62 is hardened. By adjusting the level of the arm 65 and the aperture diameter of the vanes 74 it is possible to form the acoustic lens 71 without moving the light source 69 and the lens 70. Therefore, the manufacturing system can be made simpler and the manufacturing cost can be reduced.

Figure 33:
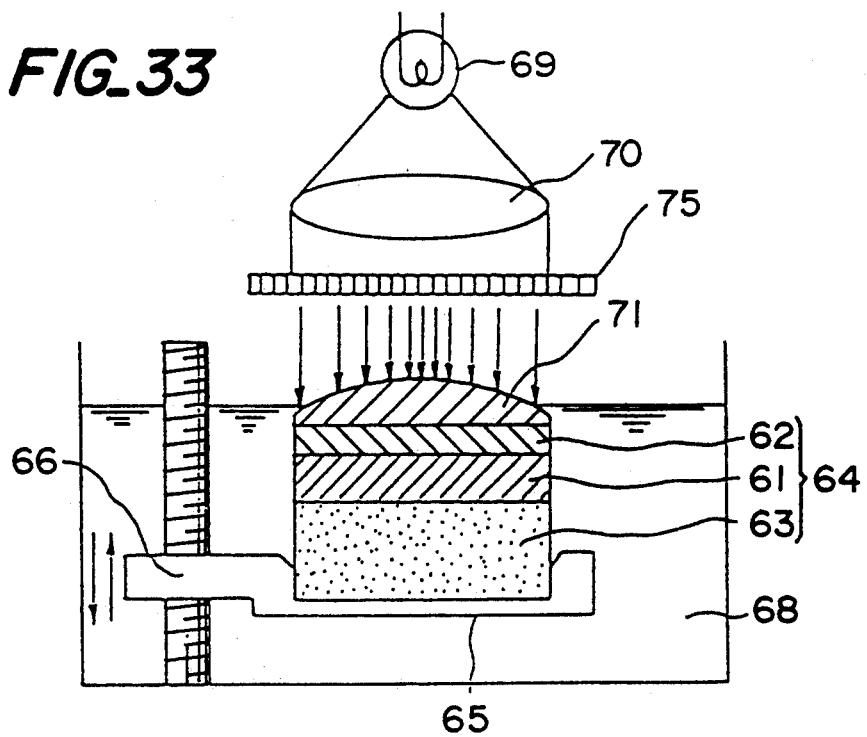

FIG. 33 is a schematic view showing a modification of the embodiment shown in FIG. 32. In the present embodiment the stop 73 having the movable vanes 74 is replaced by a liquid crystal stop 75. By using the liquid crystal stop 75 the intensity of the ultraviolet ray transmitted through the stop can be locally controlled at will, and thus various kinds of lenses such as concave lens and multi-focal point lens can be formed. Moreover the intensity of the ultraviolet ray can be adjusted without moving the optical system, so that the manufacturing system can be further made simple.

FIG. 34 is a schematic cross sectional view showing an embodiment of an apparatus for manufacturing the ultrasonic vibrator for use in the ultrasonic probe according to the invention. The ultrasonic vibrator 64 is placed in a frame member 76 and then ultraviolet setting resin liquid 78 is introduced above the matching layer 62. Next a matrix 77 having a curved surface corresponding to the curvature of an acoustic lens to be formed is inserted into the frame member 76. The matrix 77 is made of material which transmits the ultraviolet ray such as UV glass and quartz glass.

Above the matrix 77 the ultraviolet ray is made incident and the ultraviolet setting resin 78 is hardened. After that the matrix 77 is removed from the frame member 76 and then the ultrasonic vibrator with the acoustic lens formed by the hardened resin is taken out of the frame member. Finally small projections of the resin are cut off to obtain the ultrasonic vibrator shown in FIG. 35. It should be noted that the frame member 76 is used to prevent the ultraviolet setting resin from being leaked and air being introduced in the acoustic lens, but the frame member may be omitted if any. Further it is advantageous to apply the mold separating agent on the inner surfaces of the frame member and matrix.

Figure 36:
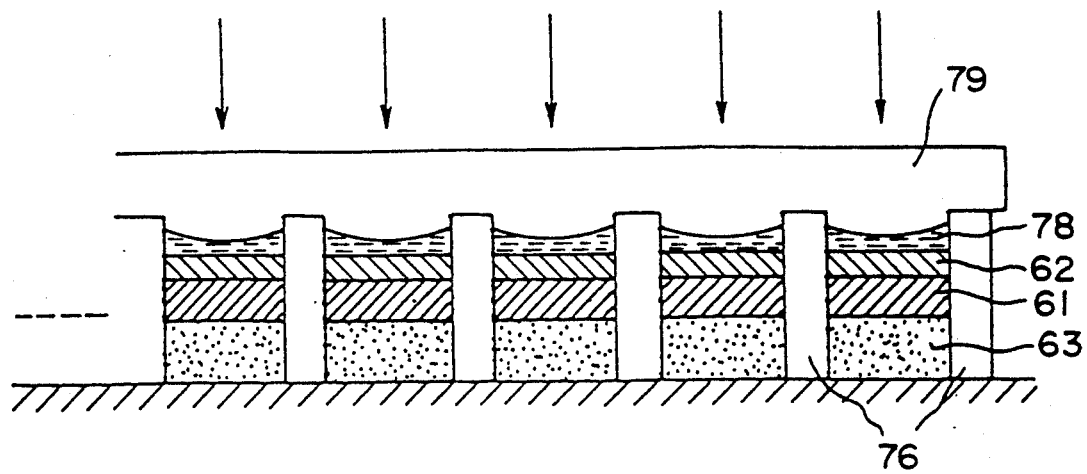
FIG. 36 and FIG. 37 are schematic views depicting sixth and seventh embodiments of the apparatus for manufacturing the acoustic lens.

FIG. 36 is a schematic view showing a sixth embodiment of the apparatus of manufacturing the ultrasonic vibrator. Similar to the second embodiment shown in FIG. 31 in the present embodiment a plurality of acoustic lenses are simultaneously formed. A plurality of ultrasonic vibrators without the acoustic lenses are placed in a plurality of frame members 76 arranged side by side. On the matching layers 62 are introduced the ultraviolet setting resin liquid 78 and after a matrix 79 having a plurality of convex portions has been inserted into the frame members, the ultraviolet ray is made incident upon the resin liquid 78 via the matrix 79 to harden the resin. In this manner a plurality of acoustic lenses can be formed simultaneously.

Figure 37:
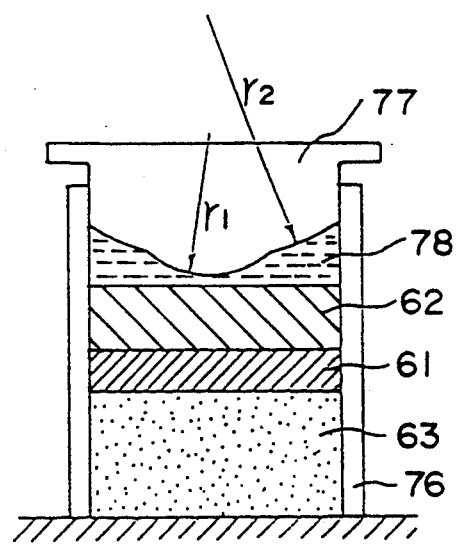

FIG. 37 is a schematic cross sectional view showing a seventh embodiment of the apparatus for manufacturing the acoustic lens. In the present embodiment, the matrix 77 has a central portion 77a having a radius of curvature $r_1$ and a peripheral portion 77b having a radius of curvature $r_2$ which is longer than $r_1$. In this manner the acoustic lens having two focal points can be formed. By using such an acoustic lens the ultrasonic wave can be focused at two different points, so that it is possible to obtain the ultrasonic image having a high resolution.

In the ultrasonic vibrators manufactured by the methods explained above, the acoustic lenses are not secured to the matching layer by the adhesive agent, but is formed integrally therewith. The acoustic lens is made of the ultraviolet setting resin which has the superior property for the transmission of the ultrasonic wave. Since the acoustic lens is integrally formed with the matching layer, the acoustic property of the lens can be improved, so that the reliability of the ultrasonic vibrator can be increased. Further the ultrasonic vibrator of small size can be manufactured easily on the large scale.

Further according to the invention, the acoustic lens is formed integrally with the acoustic matching layer from the ultraviolet setting resin having the superior acoustic property, so that the ultrasonic vibrator can have the good acoustic characteristics.

As explained above, in the ultrasonic vibrators shown in FIGS. 30 to 37, the acoustic lens is made of the ultraviolet setting resin integrally with the acoustic matching layer adhered on the piezoelectric element by means of the adhesive agent. Therefore, the acoustic property of the ultrasonic vibrator might be reduced by the unevenness of the thickness of the adhesive agent. Further the cementing operation is very cumbersome and the manufacturing cost is increased. Particularly, in case of constructing the acoustic matching layer by a stack of a plurality of matching layers having different acoustic properties, the above mentioned drawbacks become manifest. The present invention can remove such drawbacks.

FIG. 38 is a schematic view showing a first embodiment of the apparatus for manufacturing the acoustic vibrator for use in the ultrasonic vibrator according to the invention. At first a piezoelectric element 81 is held on an arm 83 of a position adjusting device 82 and is immersed in an ultraviolet setting resin liquid 85 contained in a vessel 84 as illustrated in FIG. 38A. The ultraviolet setting resin liquid 85 contains particles A mixed therewith.

Above the vessel 84 are arranged an UV light source 86 and a collimator lens 87, so that the ultraviolet ray is focused on the surface of the ultraviolet setting resin liquid 85. During the exposure of UV light ray, the position adjusting device 82 is controlled such that the surface of the piezoelectric element 81 is just below the liquid level. In this manner a thin layer of the liquid 85 is hardened and a thin layer of the hardened ultraviolet setting resin is formed. This procedure is continued while the piezoelectric element 81 is gradually descended until a first acoustic matching layer 88a having a desired thickness shown in FIG. 38B is formed.

Then the piezoelectric element 81 having the first acoustic matching layer 88a formed thereon integrally is immersed in an ultraviolet setting resin liquid 90 contained in a vessel 84 and having particles B mixed therewith. In the same manner as that of forming the first acoustic matching layer 88a, a second acoustic matching layer 88b having a desired thickness is formed on the first acoustic matching layer.

Figure 38C:
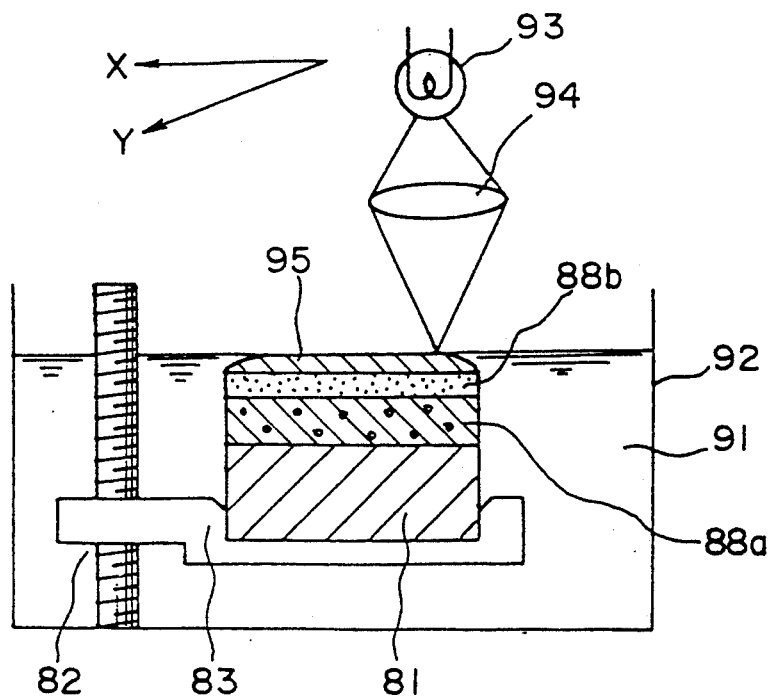

Then the piezoelectric element 81 having the first and second acoustic matching layers 88a and 88b formed integrally therewith is immersed in an ultraviolet setting resin liquid 91 contained in a vessel 92, and ultraviolet light ray is focused on the surface of the liquid to harden the ultraviolet resin as shown in FIG. 38C. The UV light source 93 and lens 94 are moved in X and Y directions by means of a suitable driving device. By controlling the position adjusting device 82 and X, Y driving device it is possible to form an acoustic lens 95 on the second acoustic matching layer 88b integrally therewith.

Figure 38D:
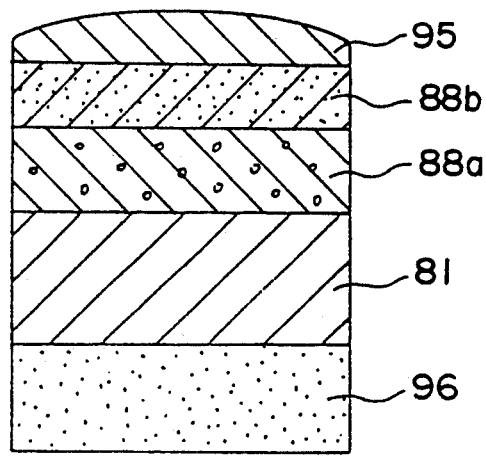

FIG. 38D depicts the ultrasonic vibrator having the first and second acoustic matching layers 88a and 88b and the acoustic lens 95 formed in the manner explained above. It should be noted that a damping layer 96 is applied on the other side of the piezoelectric element 81.

In the present embodiment, a plurality of acoustic matching layers 88a and 88b having different acoustic properties determined by the mixed particles A and B can be formed integrally with the piezoelectric element by introducing the given particles by given amounts into the ultraviolet setting resin liquid, so that it is no more necessary to secure a plurality of acoustic matching layers with the aid of the adhesive agent, so that the manufacturing efficiency can be improved. The mixed particles may be various kinds of inorganic materials such as metals, glasses and organic materials. Since the acoustic matching layers and acoustic lens are formed within the liquid the introduction of air bubbles can be effectively avoided. The driving in the X and Y directions as well as the control of the position adjusting device may be controlled by a computer.

FIG. 39 is a schematic view illustrating a second embodiment of the apparatus for forming the ultrasonic vibrator for use in the ultrasonic probe according to the invention. AT first a piezoelectric element 111 having a damping member 117 applied thereto is arranged in a space formed by a separation type mold 118. In a space within the mold 118 above the piezoelectric element 111 is filled with an ultraviolet setting resin liquid 120 having particles 119 mixed therewith. The separation type mold 118 is connected with an arm of a rotating device 121. An upper inner surface 122 of the separation type mold 118 is formed in a concave manner, so that when the ultraviolet setting resin liquid 120 is hardened by irradiating ultraviolet light ray, it is possible to form a convex acoustic lens integrally with the acoustic matching layer 111.

The rotating device 121 is driven to rotate the mold 118 and the particles 119 contained in the ultraviolet setting resin liquid 120 are dispersed by the centrifugal force to obtain a desired concentration profile.

Then the ultraviolet light ray is made incident upon the liquid 120 through the mold 118 to harden the liquid. After that the mold 118 is separated into two mold halves to obtain the ultrasonic vibrator as shown in FIG. 40.

In the present embodiment, the particles 119 contained in the ultraviolet setting resin liquid are distributed such that the concentration of the particles is decreased from the piezoelectric element 111 to the acoustic lens, so that the matching layer having the desired acoustic property can be obtained. Further the matching layer and acoustic lens are formed completely integrally with each other they are denoted by a single reference numeral 123 in FIG. 40. In this manner, the ultrasonic vibrator having good acoustic property can be manufactured in an efficient and easy manner.

FIG. 41 is a schematic view showing a third embodiment of the apparatus for forming the ultrasonic vibrator for use in the ultrasonic probe according to the invention. In the present embodiment, a piezoelectric element 111 having a damping member 117 applied on the rear surface is placed in a separation type mold 118. In a space formed within the mold above the piezoelectric element 111 is filled with an ultraviolet setting resin liquid 124 which contains magnetic and non-magnetic particles which are mixed at a desired ratio.

When a very strong magnet 125 is brought in the vicinity of the bottom of the mold 118, the magnetic particles are attracted by the magnet. Then the ultraviolet setting resin liquid 124 is hardened by irradiating ultraviolet light ray through the mold 118. After that the mold 118 is separated to obtain the ultrasonic vibrator having the acoustic matching layer and acoustic lens formed integrally with the piezoelectric element 111.

As explained above according to the invention it is possible to manufacture the ultrasonic vibrator having the acoustic matching layer and acoustic lens having good acoustic property. Further the acoustic matching layer and acoustic lens are integrally formed with the piezoelectric element, so that the cementing operation is no more required, and thus the ultrasonic vibrator having a very small size can be manufactured in a simple and less expensive manner.

In the embodiments of the ultrasonic probe according to the invention shown in FIGS. 3 to 23, the electrodes of the ultrasonic vibrator are connected to the conductors of the signal transmitting means by means of the solder, conductive adhesive agent and conductive paste. In a preferred embodiment of the ultrasonic probe according to the invention, the electrodes may be connected to the conductors with the aid of metal sponge or metal felt made of metal wool. By using such conductive members the connecting surface area becomes large and thus the connection can be obtained easily. Now several embodiments of the ultrasonic probe using such conductive members will be explained.

FIG. 42 is a cross sectional view showing a ninth embodiment of the ultrasonic probe according to the invention. In the present embodiment, on a front surface of a piezoelectric element 131 there is applied a first electrode 136 having an extended portion 136a applied on a side wall of the element 131, and on a rear surface of the piezoelectric element 131 there is applied a second electrode 136b. On the second electrode 136b is secured a backing member 132 and on the first electrode 136 there are arranged first and second acoustic matching layers 133 and 134 and an acoustic lens 135 in this order. To the side wall of the piezoelectric element 131 on which the extended electrode portion 136a is applied is secured a damping member 137 with the aid of a conductive adhesive agent. On the side wall of the backing member 132 is secured an insulating member 138 by means of an adhesive agent. To the damping member 137 is connected a first lead wire 139a and to the backing member 132 is connected a second lead wire 139b by means of solders or conductive adhesive agents 148.

The backing member 132 and damping member 137 are formed by a metal sponge or metal felt made of epoxy resin in which metal particles such as W and Ag or inorganic particles such as $WO_3$ and $Al_2O_3$. Therefore, the first and second lead wires 139a and 139b are electrically connected to the first and second electrodes 136 and 136b, respectively by means of the damping member 137 and backing member 132, respectively. Therefore, a suitable driving signal may be applied across these electrodes 136 and 136b by means of the lead wires 139a and 139b, and the piezoelectric element 131 may be actuated to generate the ultrasonic wave.

In the ninth embodiment of the ultrasonic probe explained above, the backing member 132 is formed by the material having the uniform quality and is made in contact with the piezoelectric element 131 uniformly, so that the deviation of the transmitted ultrasonic wave and undesired emission of the ultrasonic wave from the rear side can be effectively avoided. Further the lead wires may be connected after all the components have been assembled and the areas for connecting the lead wires are large, and thus the lead wire connecting operation can be carried out easily and the mechanical strength of the connecting portions can be increased.

FIG. 43 is a cross sectional view illustrating a tenth embodiment of the ultrasonic probe according to the invention. Since the construction of the present embodiment is similar to that of the previous embodiment shown in FIG. 42, only different points will be explained.

On opposite surfaces of a piezoelectric element 141 are applied first and second electrodes 146 and 146b which include extended portions 146a and 146c applied on opposite side walls of the element. On the first electrode 146 are arranged first and second acoustic matching layers 143 and 144 and acoustic lens 145 in this order, and on the second electrode 146b is applied a backing member 142.

The backing member 142 is constructed by an insulating body made of epoxy resin in which $WO_3$ or $Al_2O_3$ particles are mixed. The backing member 142 has such a dimension that it extends beyond the piezoelectric element 141, and on the extended portions of the backing member 142 are provided damping members 147a and 147b. These damping members 147a and 147b are connected to the extended portions 146a and 146c of the first and second electrodes by means of conductive adhesive agents. To the damping members 147a and 147b are connected first and second lead wires 149a and 149b, respectively with the aid of solders or conductive adhesive agents 148.

In the tenth embodiment shown in FIG. 43, the property of the backing member 142 may be determined only by considering the acoustic property, so that the optimum acoustic property can be attained. The operation of connecting the lead wires is simple and the mechanical strength of the connection points is high. Further the damping members 147a and 147b can serve to suppress undesired wave which might deteriorate the resolution of the ultrasonic image.

FIGS. 44 to 46 show an eleventh embodiment of the ultrasonic probe according to the invention. In the present embodiment, an ultrasonic vibrator 160 is formed as an array. It should be noted that each ultrasonic vibrating elements in the array has the same construction as that of the ninth embodiment illustrated in FIG. 42. That is to say, on opposite main surfaces of a piezoelectric element 151 are applied first and second electrodes 156 and 156b, the first electrode having an extended portion 156a which is applied on a side wall of the element. On the first electrode 156 are applied acoustic matching layer 153 and acoustic lens 154, and on the second electrode 156b is applied a backing member 152 by means of a conductive adhesive agent 148. Adjacent to the backing member 152 there is provided an insulating member 158 on which a damping member 157 is provided such that the damping member is brought into contact with the extended electrode portion 156a by means of a conductive adhesive agent 148.

In the present embodiment, the backing member 152 and damping member 157 are formed by a stack of conductive body 155 and insulating film 156 as shown in FIG. 45. The conductive body 155 is formed by a metal sponge or metal felt in which epoxy resin having metal particles such as W and Ag or inorganic particles such as $WO_3$ and $Al_2O_3$ mixed therewith is immersed. The backing member 152 and damping member 157 are connected to flexible print circuit boards 159a and 159b, respectively by means of conductive adhesive agents 148 such that they are isolated from each other but are electrically connected to the electrodes 156a and 156b, respectively.

In the present embodiment, the damping member may be formed by two damping members and the backing member 152 may be formed by the insulating body like as the tenth embodiment.

In the above explained ultrasonic probe of the eleventh embodiment, respective ultrasonic vibrators of the array are connected to the driving signal source (not shown) by means of the flexible print circuit boards and are driven to emit the ultrasonic wave.

In the present embodiment, the wiring to respective ultrasonic vibrating elements can be carried out after all the parts have been assembled like as the ninth and tenth embodiments, so that the wiring operation can be made simple.

As explained above in the embodiments shown in FIGS. 42 to 46, the signal transmitting means such as the lead wires and flexible print circuit boards can be easily and positively provided. Further it is not necessary to connect directly the signal transmitting means to the electrodes of the ultrasonic vibrator and more over the connecting area can be increased, so that the mechanical strength of the connection can be improved. Further since it is not necessary to form recesses or soldering portions in the backing member, the backing member can be manufactured very easily.

Further since only the backing member and acoustic matching layer are brought into contact with the piezoelectric element, the distortion of the transmitted ultrasonic wave and the inclination of the ultrasonic transmitting direction can be avoided.

Therefore, it is possible to provide the ultrasonic prove which has the high property and can be manufactured easily on the large scale.

The ultrasonic diagnosing with the aid of an ultrasonic tomographic image has been widely practiced. In the ultrasonic diagnosing apparatus, the tomographic image is displayed on a monitor screen in such manner that an ultrasonic beam is emitted towards an object, e.g. a living body to be inspected and an ultrasonic wave reflected at a portion where an acoustic impedance is changed is received.

In a conventional inserting-type ultrasonic diagnosing apparatus, an insertion section, in a distal end portion of which an ultrasonic probe is arranged, is inserted within the living body; an ultrasonic wave reflected by tissue of the living body is converted into an electric echo signal; the electric echo signal is transmitted to a driving unit arranged in a proximal side of the apparatus via a cable, which is extended through a flexible shaft arranged within the insertion section; the electric echo signal is amplified by an amplifier arranged in the driving unit; and the amplified electric echo signal is supplied to an ultrasonic observation apparatus, in which a monitor device is arranged; and the electric echo signal is converted to the ultrasonic tomographic image. For instance, in the Japanese Laid Open Patent Publication Kokai Sho No. 62-270140, is disclosed the ultrasonic diagnosing apparatus having the construction mentioned in the above.

The ultrasonic probe for use in the above mentioned ultrasonic diagnosing apparatus is required to make the outer diameter thereof as small as possible, because a pain of a patient should be decreased when the inserter section of the ultrasonic probe is inserted within the living body of the patient. Particularly, the outer diameter of the probe to be inserted within a blood vessel should be make extremely small. In such ultrasonic probes, it is required to make the outer diameter of the probe small up to about 1 mm.

In case the ultrasonic vibrator is arranged in the distal end portion of the ultrasonic probe having an extremely small outer diameter, the ultrasonic vibrator also should be made small, so that an area of the ultrasonic wave emitting surface of the ultrasonic vibrator becomes extremely small. In this case, a signal level of the electric echo signal becomes extremely low. Therefore, the electric echo signal is influenced by noise generated in a transmission path of the echo signal, and it is impossible to obtain a tomographic image having a sufficiently good quality necessary for diagnosing the living body when the tomographic image is displayed on the monitor screen of the observation apparatus.

The another object of the present invention is to provide an ultrasonic probe in which an electric echo signal having a sufficient signal level for obtaining the tomographic image of high quality can be generated even if the extremely small ultrasonic vibrator is used.

In order to attain this object, according to the present invention, in an ultrasonic probe for use in ultrasonic diagnosing constructed such that an ultrasonic wave reflected by the living body is converted to an electric echo signal by an ultrasonic vibrator and the electric echo signal is transmitted to a driving unit arranged in a proximal side of the probe and thereafter is transmitted to an observation device to display an ultrasonic tomographic image on a monitor screen; the improvement is characterized in that the ultrasonic vibrator and an amplifier for amplifying the electric echo signal are arranged one on the other in a direction of a thickness of the ultrasonic vibrator.

As described in the above, the apparatus according to the present invention, the ultrasonic vibrator and the electric signal amplifier are arranged at the top portion of the probe and are arranged one on the other in the thickness direction, and therefore, the electric signal having a sufficiently high level for obtaining a clear ultrasonic tomographic image can be obtained without making the outer diameter of the top portion of the probe larger.

FIG. 47 is a schematic view showing an internal portion of the top portion of the ultrasonic probe according to the twelfth embodiment of the present invention. A film substrate 211 is extended through the insertion section of the ultrasonic probe from the top portion of the insertion section to the driving unit. On a top portion of a front surface of the film substrate 211, is connected an IC chip 212 which constitutes a preamplifier and on a circuit surface of the IC chip 212, is connected an ultrasonic vibrator 213 including a piezoelectric element.

These elements are superimposed on the film substrate 211 and left hand edges of these elements are aligned with a top end of the film substrate 211. Since these thin plate-shaped elements are superimposed on the film substrate 211 in a thickness direction, the total thickness of these superimposed elements becomes minimum. Therefore, it is possible to mount these elements in a top portion having a small outer diameter of the insertion section of the ultrasonic probe.

These elements are electrically connected to each other in the following manner. The IC chip 212 is connected the film substrate 211 by means of bonding wires 214, on the other hand, the ultrasonic vibrator 213 is connected to the IC chip 212 by means of bumps 215. A contact method with the aid of bump is well known and widely used for mounting IC chips with a high density. That is to say, bumps are made in such manner that a tip of a gold wire having an outer diameter of about 50 $\mu$m is heated up by a torch and is melted to form a small ball of gold (bump). In this embodiment, between the IC chip 212 and the ultrasonic vibrator 213, the bumps are arranged, and the IC chip 212 is electrically connected to the ultrasonic vibrator 213 by a thermocompression bonding. The material of the bump is not limited to gold but other material having a conductivity can be used therefor.

An electric circuit comprising the ultrasonic vibrator and the amplifier can be constituted by electrically connecting these elements as mentioned in the above. In this embodiment, the total thickness of the superimposed elements can be made so small that the electronic elements can be mounted in the top portion of the insertion section of the ultrasonic probe with a high density.

FIG. 48 is a schematic view illustrating the inner parts arranged in the top portion of the inserting portion of the ultrasonic probe according to the thirteenth embodiment of the present invention. In this embodiment, the IC chip 212 and the ultrasonic vibrator 213 are arranged on both surfaces of the film substrate 211, respectively. These elements are electrically connected to each other by means of bumps 215 as explained in the above.

In this embodiment, there is formed a hole in the film substrate 211 at a portion corresponding to the back surface of the ultrasonic vibrator 213. The hole is filled with a packing material to absorb the undesired vibration generated by the ultrasonic vibrator 213. In this construction, the ultrasonic wave generated from the back side of the piezoelectric vibrator 213 is absorbed by the packing material and a direct influence is not given to the IC chip 212. In this manner the ultrasonic beam can be emitted from the ultrasonic vibrator 213 only in a desired direction.

In this embodiment, it is also possible not only to mount the electronic elements in the top portion of the insertion section of the ultrasonic probe with a high density like as the twelfth embodiment, but also to emit the ultrasonic beam with a high efficiency.

Methods of electrically contacting the IC chip with the other members will be explained in the following. Generally, the electric contact between a semiconductor element and a circuit substrate is conducted by TAB. The TAB is conducted in such manner that the semiconductor element is faced to the circuit substrate having beam leads, which are projected towards the semiconductor element from four orthogonal directions; bumps made by a conductive material such as gold, copper and soft solder are arranged on either of the semiconductor element or the beam leads of the substrate; the positions of pads formed on the semiconductor element are adjusted with respect to the positions of the beam leased of the substrate; and then the bumps are melted to make electrically contact the semiconductor element with the circuit substrate by ultrasonic bonding.

Figure 54:
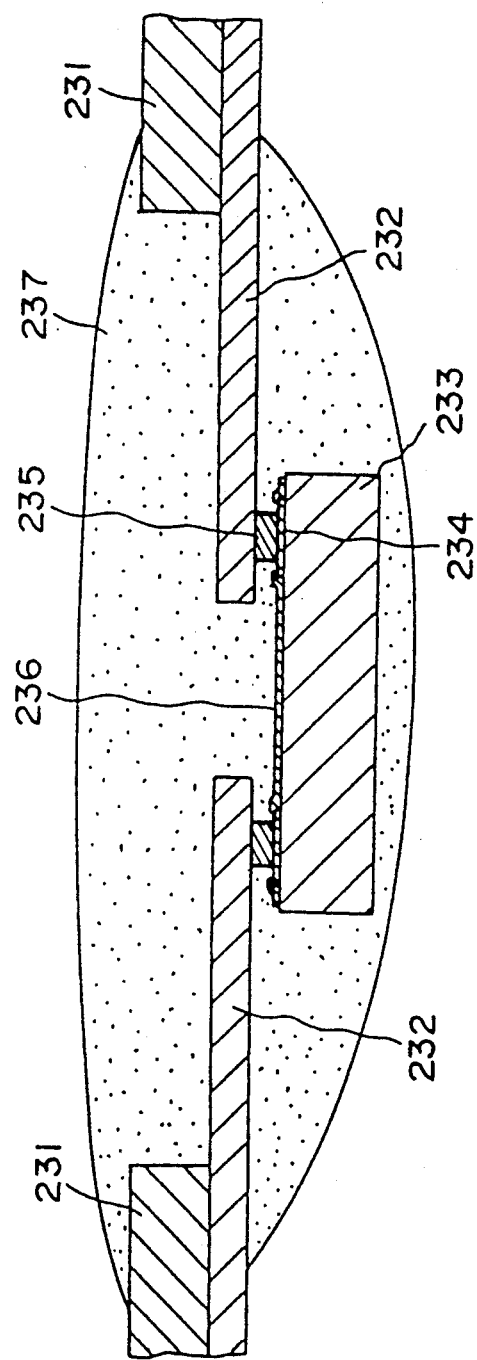
FIG. 54 is a cross sectional view illustrating the known connecting method.

FIG. 54 is a schematic view showing the conventional electric contact between semiconductor elements and beam leads of substrate used in a semiconductor device. As shown in FIG. 54, a hole is formed in a substrate 231, which is made of polyimide; a plurality of beam leads 232 are extended from four directions of the hole of the substrate to a semiconductor element 233; the semiconductor element 233 is made contact with the beam leads 232 by the ultrasonic bonding via pads 234 and projected electrodes 235 arranged in the semiconductor element 233. The numerical reference 236 denotes a passivation film provided on the semiconductor element. It should be noted that the contact point is sealed by a resin 237.

The beam leads function as contact leads for the IC chip. Each beam leads has a predetermined length and it is difficult to make the length of the beam leads short. Therefore, when the beam leads are used, a substantial space is required. Thus, the beam leads construction can not be appropriately adapted to the ultrasonic endoscope, which is required to be made the size ultra-compact. Further, when the beam leads are arranged all around the hole formed in the substrate, the polyimide substrate having a wide width is required to support the beam leads. Therefore, such beam leads construction can not be appropriately adapted to such ultrasonic endoscope of small size. Furthermore, in the ultrasonic endoscope, since the outer diameter of the top portion of the insertion section of the ultrasonic endoscope is small and the space for mounting electronic elements is rectangular, it is difficult to mount the electronic element having a lead beam construction in this space, in which the beam leads are extended from the four directions of the hole in the substrate and thus the shape of the substrate is square.

FIGS. 49A and 49B are cross sectional and plan views, respectively, depicting the fourteenth embodiment of the present invention. In this embodiment, from an edge 211a of the polyimide substrate, are extended a plurality of beam leads 220 only in one direction. On each top ends of each beam leads, is arranged a metal bump 219. It may be possible to arrange the bump 219 on the IC chip 212. In the IC chip 212, pads 217 are formed as electrode portions. After adjusting the positions of the pads 217 formed in the IC chip 212 and the bumps 219 arranged on the top portions of the beam leads 220, the beam leads 220 and the IC chip 212, which are arranged in a substantially parallel manner, are made contact with each other by the ultrasonic bonding. Thereafter, the connecting portion is sealed by the resin 221 so as to protect the IC chip. It should be noted that in FIG. 49B there is not illustrated the resin 221.

In the fourteenth embodiment, since the beam leads 220 are extended from the edge 211a of the polyimide substrate only in one direction, it is possible to mount the electronic element on the small and rectangular mounting space of the top end portion of the inserting portion of the ultrasonic probe. It should be noted that this embodiment can be adapted not only to the technical field of endoscope but also to the technical field of general semiconductor device.

FIG. 50 is a cross sectional view representing the fifteenth embodiment according to the present invention. This embodiment is a variation of the ultrasonic probe of the fourteenth embodiment explained in the above. In this embodiment, there is formed an insulating film between the beam lead 220 and the IC chip 212 a little to the polyimide substrate side by a screen printing method or a dispenser method, etc.; or there is arranged an insulator 218 between the beam lead and the IC chip 212 as represented in FIG. 50. By such construction, it is possible to prevent a short circuit between the beam lead 220 and the IC chip 212 as well as a leak of the resin 221 for use in sealing the IC chip 212.

FIGS. 51A and 51B are cross sectional and plan views of the ultrasonic probe of the sixteenth embodiment according to the invention. It should be noted that the sealing resin is omitted from these figures for the sake of clearness. In the sixteenth embodiment, a plurality of IC chips are mounted in the mounting space of the top portion of the ultrasonic probe.

FIGS. 52A and 52B are cross sectional and plan views of the seventeenth embodiment according to the invention. This embodiment is also a variation of the ultrasonic probe according to the fourteenth embodiment explained in the above. In the seventeenth embodiment, in order to hold the IC chip 212 on the beam leads 220 in a stable manner, the length of the beam leads are varied appropriately and the IC chip 212 is connected to the lead beams at two areas, i.e. in the vicinity of the front and back edges of the IC chip 212.

Figure 53A:
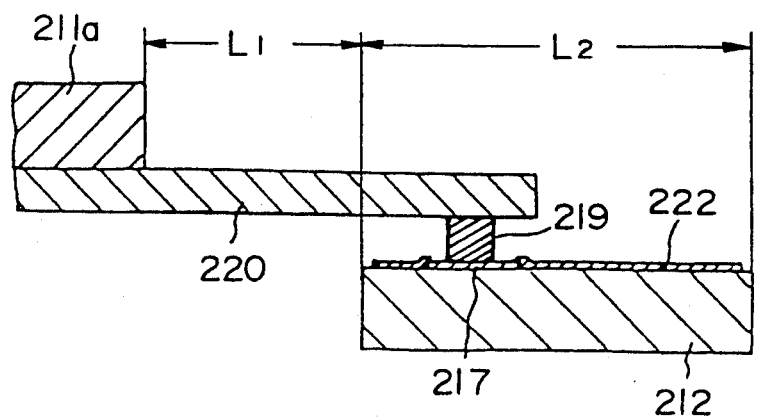
FIGS. 53A and 53B are cross sectional views showing first and second embodiments of the method of connecting the beam lead and contact pad to each other.
Figure 53B:
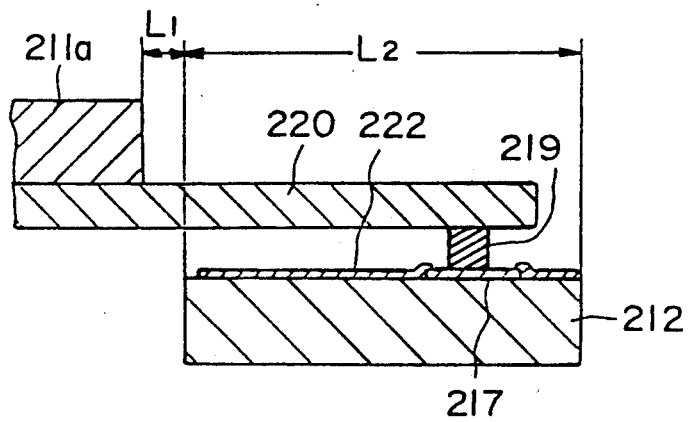

In the sixteenth and seventeenth embodiments explained in the above, the top portion of the insertion section of the ultrasonic probe as a whole can be made compact by protruding the beam leads from the substrate only in one direction. However, it is possible to make the top portion of the ultrasonic probe more compact with respect to the beam leads extending direction by arranging the electrically connecting portion of the beam lead 220 are electrically made contact with IC chip 212 as shown in FIG. 53B. That is to say, in the connecting portion of the beam lead 220 and the IC chip 212 shown in FIG. 53B, the beam lead 220 is largely superimposed on the IC chip 212 in comparison with the connecting portion shown in FIG. 53A. In the connecting portion shown in FIG. 53B, the length $L_1$ is shorter than the length $L_2$ of the connection portion shown in FIG. 53A, so that the size of the connecting portion becomes short with respect to the lead beam extending direction. The length $L_2$ is always constant.

Figure 55:
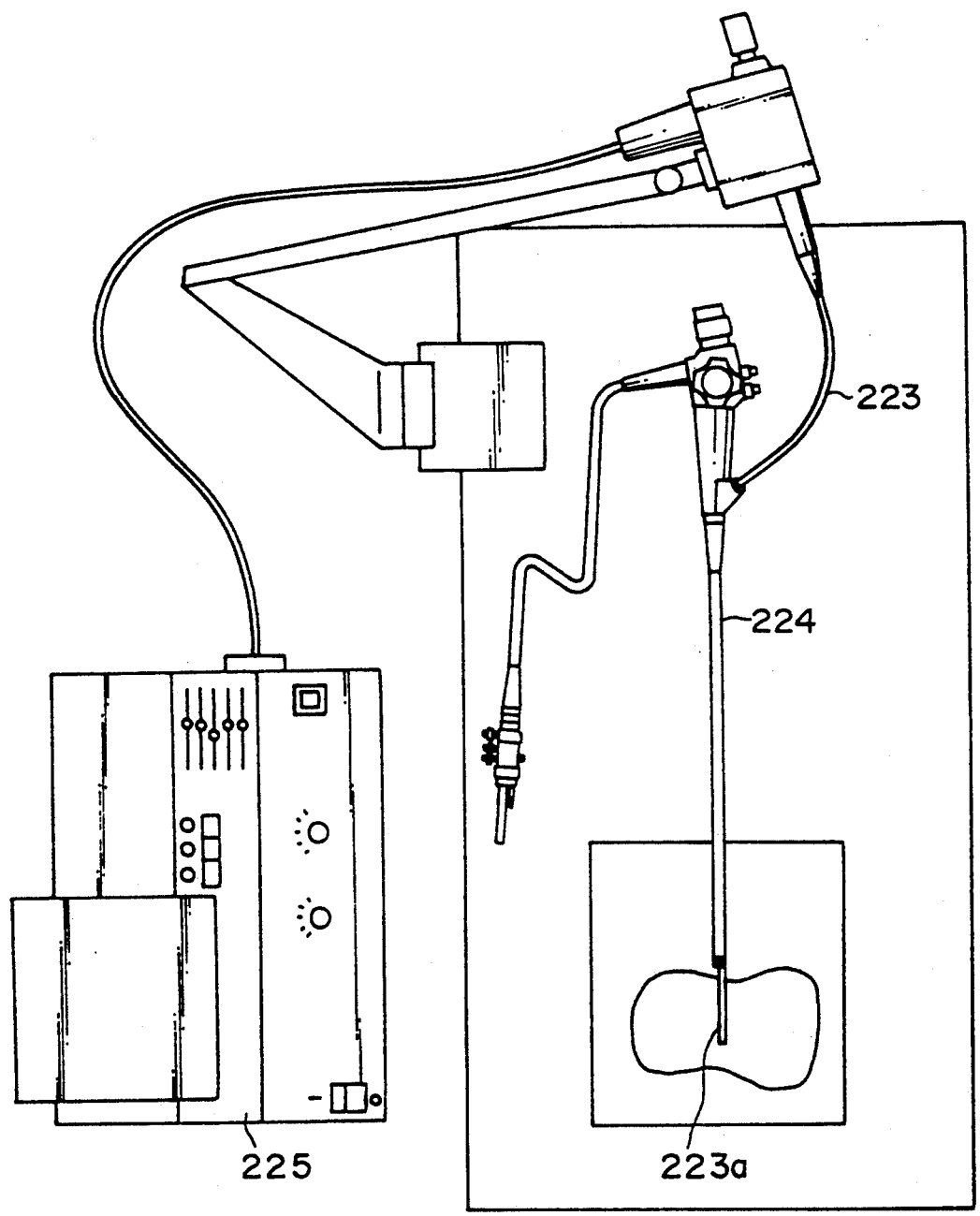
FIG. 55 is a schematic view depicting a whole construction of the ultrasonic diagnosing apparatus using the ultrasonic probe according to the invention.

The operation of the ultrasonic diagnosing apparatus, in which the ultrasonic probe according to the present invention is used, will be explained in the following on the basis of the schematic view of the apparatus as a whole illustrated in FIG. 55. A sheath 223 of the ultrasonic probe is extended through a channel arranged in the endoscope 224; and in a top end portion 223a of the sheath 223, are arranged an ultrasonic vibrator and an amplifier. The distal end portion 223a of the sheath 223 shown in FIG. 55 is inserted within the living body. When an electric voltage is applied to the piezoelectric element of ultrasonic vibrator from the ultrasonic observation apparatus 225 via a signal cable, and the piezoelectric vibrator is driven. The ultrasonic wave reflected by tissue in the living body is received by the ultrasonic vibrator and is converted to the electric echo signal thereby; and then the electric echo signal is amplified by the IC chip provided in the distal end portion 223a and is sent to the driving unit and the ultrasonic observation apparatus 225 via the signal cable.

To the ultrasonic observation apparatus 225, is sent the amplified electric echo signal. Therefore, when the amplified electric echo signal is processed in the ultrasonic observation apparatus, ultrasonic tomographic images having good quality can be obtained on the monitor screen.

Since the ultrasonic probe according to the present invention has an extremely small diameter, and the probe should be exchanged after being used about ten times. Therefore, the durability of the electronic circuit is not so large that disconnecting and cutting of wires would be generated. When the breaking of wire is generated in the electronic circuit arranged in the distal end portion of the probe, no ultrasonic tomographic image is obtained on the monitor screen of the ultrasonic observation apparatus. However, bubbles formed in the ultrasonic wave propagating liquid provided between the probe and the living body or malfunction of the amplifier arranged in the ultrasonic observation apparatus also cause the fact that no ultrasonic tomographic image is displayed on the monitor screen. Thus, it is necessary to detect whether the disconnection of wires is generated in the vicinity of the piezoelectric vibrator or not.

FIG. 56 is a block diagram depicting a circuit for detecting whether the disconnection of wires is generated or not. In this circuit, the breaking of wire is detected by detecting multiple echo signal from the sheath surrounding the piezoelectric vibrator. The piezoelectric vibrator 226 is connected to an amplifier 241 arranged in the ultrasonic observation apparatus 225 (see FIG. 52), a digital scan converter (DSC) 242 and a monitor screen 243 in this order to display the ultrasonic tomographic image on the monitor screen 243. On the other hand, the piezoelectric vibrator 226 is connected to a gate circuit 227, a comparator 228 and a light emitting diode 229, in this order.

Since the distance between the piezoelectric vibrator 226 and the sheath surrounding the piezoelectric vibrator 226 is constant, the gate circuit 227 is conducted when a trigger signal is generated by a pulsar at a predetermined time after the ultrasonic wave has been emitted from the piezoelectric vibrator; and the gated signal is compared with a predetermined reference signal being shown by a DC power supply 240 in the comparator 228. When the multiple echo signal from the sheath is detected by this circuit, the light emitting diode 229 is ignited, and thus it can be ascertained that no disconnection of wires is generated in the element.

As stated in the above, according to the twelfth to seventeenth embodiments of the present invention, since the amplifying means for amplifying the ultrasonic echo signal is arranged in the vicinity of the piezoelectric vibrator, the echo signal with a high signal level can be sent to the driving unit and the ultrasonic observation apparatus after the echo signal is amplified by the amplifying means. Therefore, it is possible to decrease the influence of noise generated in a path through which the electric signal is transmitted to the driving unit, and ultrasonic tomographic images having a sufficiently high quality necessary for diagnosing the living body can be displayed on the monitor screen.

In addition to this, each electronic element arranged in the sheath are superimposed in the thickness direction and the piezoelectric vibrator is electrically connected to the IC chip by means of the beam leads which are extended only in one direction. Therefore, these electronic elements can be mounted in the distal end portion of the ultrasonic probe with a high density but the small outer diameter of the sheath can be maintained.

In the other embodiments, in which the outer diameter of the ultrasonic probe is extremely small but echo signal necessary for ultrasonic diagnosing can be generated at the distal end portion of the ultrasonic probe, according to the invention, the piezoelectric vibrator element and a signal amplifying element are arranged in the vicinity of the distal end portion of the ultrasonic probe; and one of these elements has a function as a substrate; and the other element is mounted thereon.

Since one of the elements has a function as a substrate, the capacity for mounting elements can be saved but the echo signal having a sufficiently high level for obtaining the good ultrasonic tomographic image can be generated without making the size of the top portion of the probe large.

FIG. 57 is a schematic view illustrating electronic elements arranged in the distal end portion of the ultrasonic probe according to the eighteenth embodiment. As clear from FIG. 57, a substrate 251 comprises a thin-plate made of piezoelectric ceramics. In the substrate 251, there are provided two regions 252 and 256. On a first regions 252 is applied a high electric voltage to polarize the first region 252; and the first region 252 functions as a piezoelectric vibrator. At a center portion of one edge of one surface of the piezoelectric vibrator 252 there is provided a first electrode 253, on the other surface of the piezoelectric vibrator 252, a second electrode 254 is formed and the second electrode 254 is extended up to the surface on which the first electrode is arranged.

Further, on a second region 256, there is provided an IC chip 255 for use in the preamplifier. In this case, the IC chip 255 comprises a small thin plate; and the IC chip 255 is fixed to the surface, on which the electrodes 253 and 254 of the piezoelectric vibrator are faced to each other, of the substrate 251 such that the IC chip 255 is superimposed on the substrate in a thickness direction.

The IC chip 255 is electrically connected to the piezoelectric vibrator 252 by well known bonding wires 257 and 258.

As stated in the above, in the eighteenth embodiment, one piezoelectric ceramic element 251 constitutes the substrate 256 and the piezoelectric vibrator 252, and further the IC chip is superimposed on the piezoelectric ceramic element in a thickness direction. Therefore, the piezoelectric means and the amplifying means can be made small in sizes and thus can be mounted in the distal end portion of the ultrasonic probe.

FIG. 58 is schematic view depicting the nineteenth embodiment according to the present invention. In this embodiment, the electronic elements are mounted in the distal end portion of the ultrasonic probe with a higher density in comparison with of the eighteenth embodiment. The same numerical numbers are used for the portions corresponding to the portions of the eighteenth embodiment.

In this embodiment, a substrate 251, which is made by a thin plate of silicon chip, comprises an IC circuit 255 including the preamplifier and a piezoelectric vibrator 252. The IC circuit 255 is formed on one side of the upper surface of the substrate 251 and the piezoelectric vibrator 252 is embedded in the other side of the upper surface of the substrate 251. Electrodes 253, 254 of the piezoelectric vibrator 252 are extended to a direction of IC chip 255; and the electrodes 253, 254 are electrically connected to the IC chip 255 by means of bonding wires 257 and 258.

By the construction mentioned in the above, it is possible to mount the piezoelectric vibrating means and the amplifying means in the distal end portion of the ultrasonic probe with a higher density.

In this embodiment, the electric signal is amplified by the amplifying means arranged in the distal end portion and then sent to the ultrasonic observation apparatus. Therefore ultrasonic tomographic images having good image quality can be obtained on the monitor screen.

There are suggested two scanning systems for scanning the living body with the aid of ultrasonic wave. One of them is mechanical scanning system and the other electronical scanning system. The scanning system of the ultrasonic probe according to the present invention belongs to the former one. In the ultrasonic probe according to the invention, the piezoelectric vibrator arranged in the distal end portion of the probe is rotated with respect to the radial direction to scan the living body; and when the ultrasonic beam is emitted to the external portion, the portion surrounding the piezoelectric vibrator is filled with an acoustic wave propagating medium so that the ultrasonic beam can be propagated to the living body through an acoustic window.

The piezoelectric vibrator is rotated with respect to the radial direction in such manner that the driving power of the motor arranged in the driving unit, which is arranged in the proximal portion of the ultrasonic diagnosing apparatus, is transmitted to the piezoelectric vibrator via the flexible shaft extending from the proximal portion to the piezoelectric vibrator through the inserting portion of the apparatus. The flexible shaft is constituted by helical springs, etc. and is rotated with respect to the radial direction in the sheath, which is made of Teflon. Therefore, a friction is surely caused by a contact of the inner wall of the sheath and the outer surface of the flexible shaft. If the friction force generated therebetween is large, the piezoelectric vibrator arranged at the distal top end of the flexible shaft could not be rotated smoothly, and the ultrasonic beam could not be sent to and received by the driving unit correctly because of unevenness of the rotation of the piezoelectric vibrator.

FIG. 59 is a schematic view showing a construction of the sheath by which the problem mentioned in the above can be solved. The flexible shaft 260 is inserted into the sheath 259; a sliding member 261 is wound around the outer surface of the flexible shaft 260 in a spiral manner so that the outer surface of the flexible shaft is not made contact with the inner surface of the sheath 259 but only the sliding member 261 is made contact with the inner surface of the sheath 259. In such construction, it is possible to decrease the frictional force between the outer surface of the flexible shaft 260 and the inner surface of the sheath 259 even if the flexible shaft 260 is rotated in the sheath 259 with respect to the radial direction. It should be noted that carbon, Teflon, etc. are preferred as the material for the sliding member 261, and the material may be selected taking under consideration of the material of the sheath 259.

As explained in the above, according to the eighteenth and nineteenth embodiments of the present invention, although the extremely small piezoelectric vibrator is arranged in the extremely small distal end portion, it is possible to suppress the influence of noise generated in the signal transmitting path, because the ultrasonic echo signal is transmitted to the ultrasonic observation apparatus after the echo signal is amplified by the amplifying means arranged in the vicinity of the piezoelectric vibrator. Therefore, it is possible to obtain ultrasonic tomographic images having good image quality, so that accurate diagnosis can be carried out by monitoring the ultrasonic images displayed on the monitor screen.

Further to the above, according to these embodiments, one of the electronic elements serves as a substrate of another element, and thus the capacity for mounting electronic elements can be made small. Such elements are mounted in the small capacity with a high density, so that the extremely small diameter of the sheath can be realized.

Other embodiment, in which the ultrasonic vibrator and the amplifying element are mounted at the distal end portion of the ultrasonic probe, will be explained in below. In this embodiment, the ultrasonic vibrator is electrically connected to an IC chip and the ultrasonic vibrator and the IC chip are molded as a single body by an insulating material as a housing.

FIG. 60 is a schematic view showing the internal portion of the distal end portion of the insertion section of the ultrasonic probe according to the twentieth embodiment, in which the ultrasonic vibrator and the IC chip are molded as a single body by means of the insulating housing. The ultrasonic vibrator 271 comprises a thin plate having a small area; the ultrasonic vibrator 271 is superimposed on the IC chip 272 in a thickness direction and these elements are electrically contact with each other.

The ultrasonic vibrator 271 is made contact with the IC chip 272 by thermocompression bonding by means of bumps 273 arranged between the ultrasonic vibrator 271 and the IC chip 272. In the ultrasonic vibrator 271, a negative electrode 280 is formed on the main surface and the electrode 280 is extended to on one part of the opposite surface thereof via one of the side surfaces thereof; and a positive electrode 281 is formed on the other part of the opposite surface of the ultrasonic vibrator 271. The ultrasonic vibrator 271 is vibrated by electric current supplied from a power supply arranged in the proximal end of the ultrasonic probe to emit the ultrasonic beam.

The IC chip 272 is arranged in an opposite side of the ultrasonic beam emitting surface of the ultrasonic vibrator 271. The IC chip 272 serves as a preamplifier for amplifying an echo signal generated by the ultrasonic vibrator 271. The numerical number 274 denotes the signal cable extending within the sheath of the ultrasonic probe.

The elements 271, 272 and top portion of the signal cable 274 are integrally molded by a housing 278 made of plastic material in order to connect these elements and the signal cable in more strong manner and to constitute the electric circuit without substrate. Further to this, the plastic material also serves as a damper of the ultrasonic vibrator 271. Furthermore, since the elements 271 and 272 are arranged in the housing 278, the holding member for holding the elements is not necessary. It is a matter of course that the ultrasonic wave emitting surface of the ultrasonic vibrator 271 should be exposed to an external of the housing 278.

In such construction of the ultrasonic probe, the piezoelectric vibrating means and the signal amplifying means can be mounted in the top portion of the ultrasonic probe with a high density and the manufacturing efficiency and the reliability of the ultrasonic probe can be increased.

FIGS. 61A and 61B are perspective and cross section views illustrating an internal portion 276b of the distal end portion of the sheath 276 which is used in the ultrasonic probe according to the present invention. In a conventional ultrasonic probe with a guide wire, a first channel is formed in an extending direction through a catheter and a second channel is formed therein in parallel with the first channel; and the guide wire is extended through the first channel and the flexible shaft is extended through the second channel, at the distal end of the flexible shaft is arranged the ultrasonic vibrator. Therefore, the thickness of the tube wall of the ultrasonic probe in the vicinity of the distal end portion where the ultrasonic vibrator is arranged is not uniform. In case the ultrasonic vibrator is rotated with respect to the radial direction to scan the living body with the aid of ultrasonic wave, the scanning would not be conducted in a uniform condition or unnecessary echo would be caused because the ultrasonic beam would be emitted and received through the tube having the uneven thickness.

In the embodiment illustrated in FIGS. 61A and 61B, the housing 278, in which the ultrasonic vibrator is arranged, is made compact; and in the housing 278 only the ultrasonic vibrator is arranged, so that the thickness of the tube wall, through which the ultrasonic beam is emitted and received, is made uniform. The lumen 282 of the channel for use in the guide wire is arranged to be deviated from the position of housing 278 to the proximal side. In such structure, the distal end portion 276a of the probe can be made smaller and the thickness of the tube wall surrounding the ultrasonic vibrator 271 can be made uniform.

As stated in the above, according to the twentieth embodiment of the present invention, the extremely small piezoelectric vibrator is arranged in the distal end portion of the ultrasonic probe having an extremely small outer diameter; and the echo signal is supplied to the ultrasonic wave observation apparatus after being amplified by the amplifying means arranged in the vicinity of the piezoelectric vibrator without being influenced by the noise generated in the ultrasonic wave transmitting path, and therefore, it is possible to obtain ultrasonic tomographic images having sufficiently high quality necessary for diagnosing the living body, on the monitor screen.

Furthermore, in the ultrasonic probe according to the twentieth embodiment, since the elements arranged in the distal end portion of the ultrasonic probe are fixed to each other by a plastic material, which serves as a housing, the elements can be mounted in the distal end portion with a high density without a substrate. Therefore, it is possible to make the outer diameter of the distal end portion of the ultrasonic probe much smaller.

What is claimed is:

1. An ultrasonic probe comprising:

an ultrasonic vibrator for transmitting and receiving an ultrasonic wave including a piezoelectric element and first and second electrodes each applied on opposite main surfaces of the piezoelectric element;

supporting means for supporting said ultrasonic vibrator such that the ultrasonic wave transmitted by the ultrasonic vibrator is directed towards an object under inspection and the ultrasonic wave reflected by the object is received by the ultrasonic vibrator;

a signal transmitting means arranged integrally with said supporting means for transmitting a driving signal for the ultrasonic vibrator and an echo signal generated by the ultrasonic vibrator; and connecting means for connecting said signal transmitting means to said first and second electrodes of the ultrasonic vibrator; and wherein said supporting means comprises a housing which is made of insulating material and which includes a first recess and recessed connecting areas formed in a surface thereof, said connecting areas being in communication with said first recess and having a depth which is smaller than that of said first recess, said ultrasonic vibrator being inserted in said first recess such that portions of said first and second electrodes are exposed within the connecting areas of said second recess, said signal transmitting means comprises first and second conductors whose tips are exposed within said connecting areas, said connecting means comprises first and second conductive members for connecting said tips of the first and second conductors to said first and second electrodes, respectively, and said first and second conductive members are covered with an insulating layer.

2. An ultrasonic probe according to claim 1, wherein said first and second conductive members are formed by a conductive material selected from a group consisting of solder, conductive paste and conductive adhesive agent.

3. An ultrasonic probe according to claim 1, wherein said portions of said first and second electrodes of the ultrasonic vibrator are extended over opposite side walls of the piezoelectric element, exposed within the connecting areas and are connected to said first and second conductors, respectively by means of said first and second conductive members, respectively.

4. An ultrasonic probe according to claim 3, wherein said housing is formed substantially in a cylindrical shape.

5. An ultrasonic probe according to claim 4, wherein said first and second conductors are extended from the same one end face of the cylindrical housing.

6. An ultrasonic probe according to claim 5, wherein the other end face of the cylindrical housing is formed substantially in a conical shape.

7. An ultrasonic probe according to claim 1, wherein said housing is formed by a mold of insulating material.

8. An ultrasonic probe according to claim 1, wherein said housing further comprises depressions formed in boundaries of the recess and the connecting areas such that said depressions serve to contain overflowed adhesive agents for securing the ultrasonic vibrator to the recess.

9. An ultrasonic probe according to claim 4, wherein said signal transmitting means comprises first and second lead wires, said connecting means comprises first and second conductive members for connecting said first and second lead wires to the first and second electrodes, respectively of the ultrasonic vibrator, and said lead wires are extended from the supporting means and are connected to a connector.

10. An ultrasonic probe according to claim 4, wherein said ultrasonic vibrator further comprises at least one acoustic matching layer applied on the first electrode.

11. An ultrasonic probe according to claim 10, the ultrasonic vibrator further comprises an acoustic lens applied on the acoustic matching layer.

12. An ultrasonic probe according to claim 11, wherein said acoustic matching layer and acoustic lens are integrally formed by an insulating layer which covers the connecting means.

13. An ultrasonic probe according to claim 10, wherein said acoustic matching layer is formed by an insulating layer which covers the connecting means.

14. An ultrasonic probe according to claim 4, wherein a preamplifier for amplifying the echo signal generated by the ultrasonic vibrator is provided on the supporting means.

15. An ultrasonic probe according to claim 14, wherein said preamplifier is arranged in a direction of a width of the ultrasonic vibrator.

16. An ultrasonic probe comprising:
an ultrasonic vibrator for transmitting and receiving an ultrasonic wave including a piezoelectric element and first and second electrode each applied on opposite main surfaces of the piezoelectric element;
supporting means for supporting said ultrasonic vibrator such that the ultrasonic wave transmitted by the ultrasonic vibrator is directed towards an object under inspection and the ultrasonic wave reflected by the object is received by the ultrasonic vibrator;
a signal transmitting means arranged integrally with said supporting means for transmitting a driving signal for the ultrasonic vibrator and an echo signal generated by the ultrasonic vibrator; and
connecting means for connecting said signal transmitting means to said first and second electrodes of the ultrasonic vibrator, and wherein said supporting means comprises a housing which is made of electrically conductive material and which includes a recess formed in a surface thereof, the ultrasonic vibrator is secured to the recess by means of a backing member, said signal transmitting means comprises a coaxial cable having a core conductor and a shielding conductor covering the core conductor, and said connecting means comprises a first conductive member for connecting the core conductor to the first electrode of the ultrasonic vibrator, a second conductive member for connecting the second electrode of the ultrasonic vibrator to the housing and a third conductive member for connecting the shielding conductor to the housing.

17. An ultrasonic probe according to claim 16, wherein said first electrode includes an extended portion which extends to cover one side wall of the ultrasonic vibrator, said second electrode includes an extended portion which extends to cover the other side wall of the ultrasonic vibrator, said core conductor is connected to said extended portion of the first electrode by the first conductive member, and said extended portion of the second electrode is connected to the housing by the second conductive member.

18. An ultrasonic probe according to claim 17, wherein said backing member includes an insulating member provided at a portion at which the extended portion of the first electrode is brought into contact with the backing member.

19. An ultrasonic probe according to claim 18, wherein said housing has a hole formed therein near said one side wall of the ultrasonic vibrator, the shielding conductor is inserted into said hole, and the shielding conductor is connected to the housing by the third conductive member within said hole.

20. An ultrasonic probe according to claim 18, wherein said backing member is made of electrically conductive material.

21. An ultrasonic probe comprising:
an ultrasonic vibrator for transmitting and receiving an ultrasonic wave including a piezoelectric element and first and second electrodes each applied on opposite main surfaces of the piezoelectric element;
supporting means for supporting said ultrasonic vibrator such that the ultrasonic wave transmitted by the ultrasonic vibrator is directed towards an object under inspection and the ultrasonic wave reflected by the object is received by the ultrasonic vibrator;
a signal transmitting means arranged integrally with said supporting means for transmitting a driving signal for the ultrasonic vibrator and an echo signal generated by the ultrasonic vibrator; and
connecting means for connecting said signal transmitting means to said first and second electrode of the ultrasonic vibrator, wherein said supporting means comprises a recess in which said ultrasonic vibrator is inserted and fixed, said signal transmitting means comprises a flexible print circuit board having first and second conductive patterns, and said connecting means comprises first and second conductive members for connecting the first and second electrodes of the ultrasonic vibrator to the first and second conductive patterns, respectively, of the print circuit board.

22. An ultrasonic probe according to claim 21, wherein said supporting means comprises means comprises a substantially cylindrical housing, a portion of which is cut off to form a flat surface in which said recess is formed, and said print circuit board is cemented onto said flat surface.

23. An ultrasonic probe comprising:

an ultrasonic vibrator for transmitting and receiving an ultrasonic wave including a piezoelectric element and first and second electrodes each applied on opposite main surfaces of the piezoelectric element;

supporting means for supporting said ultrasonic vibrator such that the ultrasonic wave transmitted by the ultrasonic vibrator is directed towards an object under inspection and the ultrasonic wave reflected by the object is received by the ultrasonic vibrator;

a signal transmitting means arranged integrally with said supporting means for transmitting a driving signal for the ultrasonic vibrator and an echo signal generated by the ultrasonic vibrator; and connecting means for connecting said signal transmitting means to said first and second electrodes of the ultrasonic vibrator, wherein said ultrasonic vibrator further comprises at least one acoustic matching layer applied on the first electrode and said acoustic matching layer is formed integrally with the first electrode by means of an ultraviolet setting resin.

24. An ultrasonic probe according to claim 10, wherein said acoustic lens is formed integrally with the acoustic matching layer by means of an ultraviolet setting resin.

25. An ultrasonic probe comprising:

an ultrasonic vibrator for transmitting and receiving an ultrasonic wave including a piezoelectric element and first and second electrodes each applied on opposite main surfaces of the piezoelectric element;

supporting means for supporting said ultrasonic vibrator such that the ultrasonic wave transmitted by the ultrasonic vibrator is directed towards an object under inspection and the ultrasonic wave reflected by the object is received by the ultrasonic vibrator;

a signal transmitting means arranged integrally with said supporting means for transmitting a driving signal for the ultrasonic vibrator and an echo signal generated by the ultrasonic vibrator; and connecting means for connecting said signal transmitting means to said first and second electrodes of the ultrasonic vibrator, wherein said ultrasonic vibrator further comprises at least one acoustic matching layer applied on the first electrode and said acoustic matching layer and said acoustic lens are formed integrally with the first electrode of the ultrasonic vibrator by means of an ultraviolet setting resin.

26. An ultrasonic probe comprising:

an ultrasonic vibrator for transmitting and receiving an ultrasonic wave including a piezoelectric element and first and second electrodes each applied on opposite main surfaces of the piezoelectric element;

supporting means for supporting said ultrasonic vibrator such that the ultrasonic wave transmitted by the ultrasonic vibrator is directed towards an object under inspection and the ultrasonic wave reflected by the object is received by the ultrasonic vibrator;

a signal transmitting means arranged integrally with said supporting means for transmitting a driving signal for the ultrasonic vibrator and an echo signal generated by the ultrasonic vibrator; and connecting means for connecting said signal transmitting means to said first and second electrodes of the ultrasonic vibrator, wherein said connecting means comprises first and second conductive members made of metal sponge or metal felt and arranged to be brought into contact with the first and second electrodes of the ultrasonic vibrator, respectively, and third and fourth conductive members for connecting the first and second conductive members to first and second conductors, respectively to the signal transmitting means.

27. An ultrasonic probe according to claim 26, wherein said first and second conductive members are arranged to absorb undesired ultrasonic wave emitted form the ultrasonic vibrator.

* * * * *